United States Patent
Li et al.

(10) Patent No.: US 11,072,599 B2
(45) Date of Patent: Jul. 27, 2021

(54) PYRAZOLE COMPOUNDS AND USES THEREOF

(71) Applicant: Yissum Research Development Company of the Hebrew University of Jerusalem Ltd., Jerusalem (IL)

(72) Inventors: Dansu Li, Warrington, PA (US); Irit Snir-Alkalay, Mevasseret Zion (IL); Joseph Vacca, Telford, PA (US); Yinon Ben-Neriah, Mevasseret Zion (IL); Avanthika Venkatachalam, Jerusalem (IL)

(73) Assignee: BioTheryX, Inc., Chappaqua, NY (US)

( * ) Notice: Subject to any disclaimer, the term of this patent is extended or adjusted under 35 U.S.C. 154(b) by 0 days.

(21) Appl. No.: 16/482,199

(22) PCT Filed: Jan. 30, 2018

(86) PCT No.: PCT/IL2018/050100
§ 371 (c)(1),
(2) Date: Jul. 30, 2019

(87) PCT Pub. No.: WO2018/142393
PCT Pub. Date: Aug. 9, 2018

(65) Prior Publication Data
US 2020/0354340 A1 Nov. 12, 2020

Related U.S. Application Data

(60) Provisional application No. 62/453,192, filed on Feb. 1, 2017.

(51) Int. Cl.
| | | |
|---|---|---|
| C07D 401/04 | (2006.01) | |
| C07D 403/04 | (2006.01) | |
| C07D 471/04 | (2006.01) | |
| A61K 31/4439 | (2006.01) | |
| A61K 31/506 | (2006.01) | |
| A61K 31/4155 | (2006.01) | |
| A61K 31/427 | (2006.01) | |
| A61P 35/00 | (2006.01) | |
| C07D 403/14 | (2006.01) | |
| C07D 417/04 | (2006.01) | |

(52) U.S. Cl.
CPC ......... *C07D 403/04* (2013.01); *C07D 401/04* (2013.01); *C07D 403/14* (2013.01); *C07D 417/04* (2013.01)

(58) Field of Classification Search
CPC .. C07D 401/04; C07D 403/04; C07D 471/04; A61K 31/4439; A61K 31/506; A61K 31/4155; A61K 31/427; A61P 35/00
See application file for complete search history.

(56) References Cited

U.S. PATENT DOCUMENTS

| | | |
|---|---|---|
| 10,376,511 B2 | 8/2019 | Ben Neriah et al. |
| 2015/0094305 A1 | 4/2015 | Romero et al. |
| 2015/0202205 A1 | 7/2015 | Baldino et al. |

FOREIGN PATENT DOCUMENTS

| | | |
|---|---|---|
| EP | 2651405 | 10/2013 |
| RU | 2604062 C2 | 12/2016 |
| WO | 2007/129195 A2 | 11/2007 |
| WO | 2015/058140 A2 | 4/2015 |
| WO | 2016/081679 A1 | 5/2016 |
| WO | 2016081679 A1 | 5/2016 |
| WO | 2016/149756 A1 | 9/2016 |
| WO | 2016149756 A1 | 9/2016 |
| WO | 2017/021969 A1 | 2/2017 |
| WO | 2017021969 A1 | 2/2017 |

OTHER PUBLICATIONS

Adams et al., "IRAK1 is a novel DEK transcriptional target and is essential for head and neck cancer cell survival," Oncotarget 2015, 6:43395-43407.
Amit et al., "Axin-mediated CKI phosphorylation of beta-catenin at Ser 45: a molecular switch for the Wnt pathway," Genes Dev. 2002, 16:1066-1076.
Aran et al., "Widespread parainflammation in human cancer," Genome Biol. 2016, 17:145.
Bahia et al., "Interleukin-1 receptor associated kinase inhibitors: potential therapeutic agents for inflammatory- and immune-related disorders," Cell Signal. 2015, 27:1039-1055.
(Continued)

*Primary Examiner* — Bruck Kifle
(74) *Attorney, Agent, or Firm* — Lin Yu, Esq.; Juniv LLP

(57) ABSTRACT

The present invention provides pyrazole derivatives of Formula (I), and in particular N1-(4-(5-(cyclopropylmethyl)-1-methyl-1H-pyrazol-4-yl) pyridin-2-yl)cyclohexane-1,4-diamine derivatives and related compounds as casein kinase 1 (CK1) and/or interleukin 1 receptor associated kinase 1 (IRAK1) inhibitors for treating cancer, inflammatory and immune related disorders.

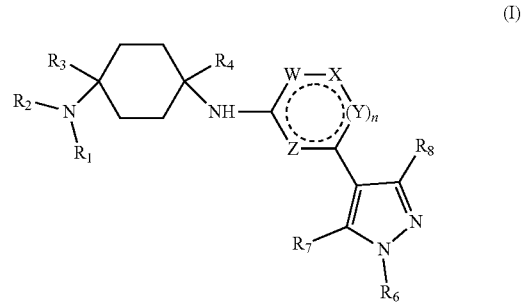

(I)

25 Claims, 1 Drawing Sheet

(56) References Cited

OTHER PUBLICATIONS

Berge et al., "Pharmaceutical salts," J. Pharm. Sci. 1977, 66:1-19.
Cheong et al., "Casein kinase 1: Complexity in the family," Int. J. Biochem. Cell Biol. 2011, 43:465-469.
Clevers et al., "Wnt/β-catenin signaling and disease," Cell 2012, 149:1192-1205.
Duan et al., "mTOR generates an auto-amplification loop by triggering the βTrCP- and CK1α-dependent degradation of DEPTOR," Mol. Cell 2011, 44:317-324.
Elyada et al., "CK1α ablation highlights a critical role for p53 in invasiveness control," Nature 2011, 470:409-413.
Fabian et al., "A small molecule-kinase interaction map for clinical kinase inhibitors," Nat. Biotechnol. 2005, 23:329-336.
Fish et al., "Isolation and characterization of human casein kinase I epsilon (CKI), a novel member of the CKI gene family," J. Biol. Chem. 1995, 270:14875-14883.
Karaman et al., "A quantitative analysis of kinase inhibitor selectivity," Nat. Biotechnol. 2008, 26:127-132.
Knippschild et al., "The casein kinase 1 family: participation in multiple cellular processes in eukaryotes," Cell Signal 2005, 17:675-689.
Lasry et al., "Senescence-associated inflammatory responses: aging and cancer perspectives," Trends Immunol. 2015, 36:217-228.
Pribluda et al., "A senescence-inflammatory switch from cancer-inhibitory to cancer-promoting mechanism," Cancer Cell 2013, 24:242-256.
Rhyasen et al., "Targeting IRAK1 as a therapeutic approach for myelodysplastic syndrome," Cancer Cell 2013, 24:90-104.
Rhyasen et al., "Differential IRAK signaling in hematologic malignancies," Exp. Hematol. 2013, 41:1005-1007.
Sansom et al., "Loss of Apc in vivo immediately perturbs Wnt signaling, differentiation, and migration," Genes Dev. 2004, 18:1385-1390.
Schittek et al., "Biological functions of casein kinase 1 isoforms and putative roles in tumorigenesis," Mol. Cancer 2014, 13:231.
Wee et al., "IRAK1 is a therapeutic target that drives breast cancer metastasis and resistance to paclitaxel," Nat. Commun. 2015, 6:8746.
Zemp et al., "CK1σ and CK1ε are components of human 40S subunit precursors required for cytoplasmic 40S maturation," J. Cell Sci. 2014, 127:1242-1253.

Adams et al., "IRAK1 is a novel DEK transcriptional target and is essential for head and neck cancer cell survival," Oncotarget. 2015, 6, 43395-407.
Amit et al., "Axin-mediated CKI phosphorylation of β-catenin at Ser 45: a molecular switch for the Wnt pathway," Genes Dev. 2002, 16, 1066-76.
Bahia et al., "Interleukin-1 receptor associated kinase inhibitors: Potential therapeutic agents for inflammatory- and Immune-related disorders," Cell. Signal. 2015, 27, 1039-55.
Cheong and Virshup, "Casein kinase 1: complexity in the family," J. Biochem. Cell Biol., 2011, 43, 465-69.
Clevers and Nusse, "Wnt/β-catenin signaling and disease," Cell 2012, 149, 1192-205.
Duan et al., "mTOR generates an auto-amplification loop by triggering the βTrCP- and CK1α-dependent degradation of DEPTOR," Mol. Cell 2011, 44, 317-24.
Elyada et al., "CK1α ablation highlights a critical role for p53 in invasiveness control," Nature, 2011, 470, 409-13.
Fish et al., "Isolation and characterization of human casein kinase I epsilon (CKI), a novel member of the CKI gene family," J. Biol. Chem. 1995, 270, 14875-83.
Knippschild et al., "The casein kinase 1 family: participation in multiple cellular processes in eukaryotes," Cell. Signal. 2005, 17, 675-89.
Lasry and Ben-Neriah, "Senescence-associated inflammatory responses: aging and cancer perspectives," Trends Immunol. 2015, 36, 217-28.
Pribluda et al., "A senescence-inflammatory switch from cancer-inhibitory to cancer-promoting mechanism," Cancer Cell 2013, 24, 1-5.
Rhyasen et al., "Differential IRAK signaling in hematologic malignancies," Exp. Hematol. 2013, 41, 1005-7.
Sansom et al., "Loss of Apc in vivo immediately perturbs Wnt signaling, differentiation, and migration," Genes Dev. 2004, 18, 1385-90.
Schittek and Sinnberg., "Biological functions of casein kinase 1 isoforms and putative roles in tumorigenesis," Mol. Cancer. 2014, 13, 231.
Zemp, et al., "CK1σ and CK1ε are components of human 40S subunit precursors required for cytoplasmic 40S maturation," J. Cell Sci. 2014, 127, 1242-53.
Belikov, "Relationship between the chemical structure, properties of substances and their effect on the body." In Pharmaceutical Chemistry; Belikov Ed; MEDpress-inform, 2007; pp. 27-29.
Rospatent's order of Jul. 25, 2011, No. 87 "On the introduction of the Guide to the Examination of Applications for Inventions".

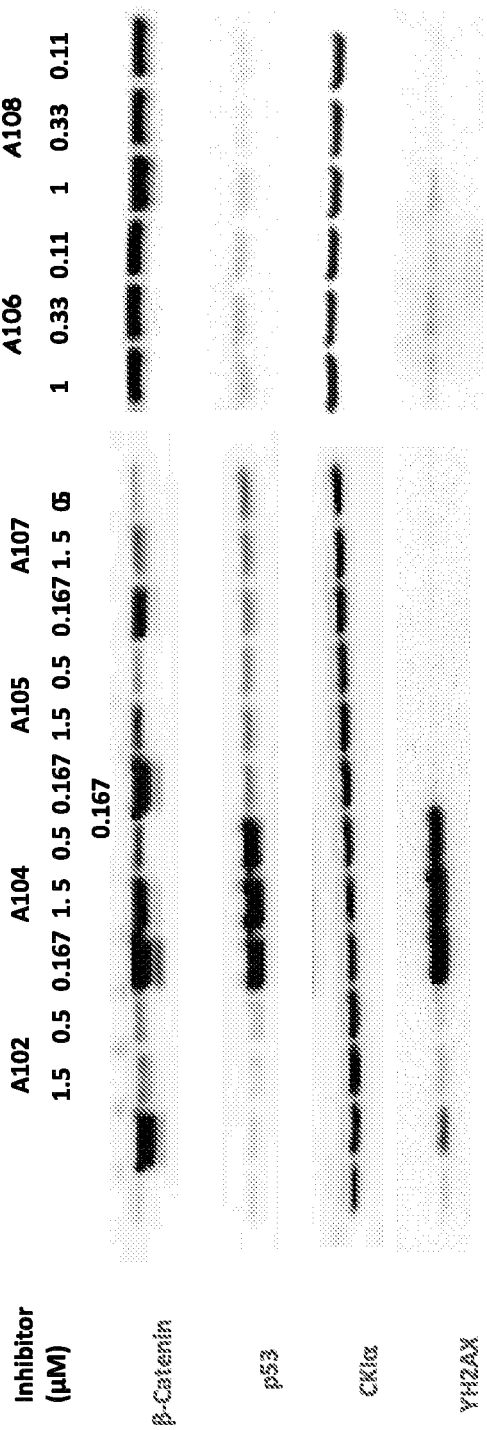

PYRAZOLE COMPOUNDS AND USES THEREOF

CROSS REFERENCE TO RELATED APPLICATIONS

This application is a National Stage of International Application No. PCT/IL2018/050100, filed Jan. 30, 2018; which claims the benefit of the priority of U.S. Provisional Application No. 62/453,192, filed Feb. 2, 2017; the disclosure of each of which is incorporated herein by reference in its entirety.

TECHNOLOGICAL FIELD

The present invention provides pyrazole derivatives and uses thereof in methods of treating malignant disease and disorders and methods for treating inflammatory diseases and disorders.

BACKGROUND

The casein kinase 1 family (CK1 or CKI) are serine/threonine kinases with six members (isoforms) in humans: α, γ1, γ2, γ3, δ and ε. They differ in length and sequence of the N-terminal (9-76 amino acids) and especially the C-terminal (24-200 amino acids) non-catalytic domain (Schittek and Sinnberg, *Mol. Cancer* 2014, 13:231).

CK1δ and CK1ε are 98% identical in their kinase domain and 53% identical in their C-terminal regulatory domain (Fish et al., *J. Biol. Chem.* 1995, 270:14875-14883). Whereas, there is some redundancy with respect to CK1 substrate phosphorylation, most CK1 isoforms have distinct biological roles. The wide range of CK1 substrates shows that the CK1 family members are involved in multiple cellular processes, from regulation of membrane trafficking, cytokinesis, vesicular transport, ribosome biogenesis, DNA repair, signal transduction pathways, apoptosis and in the circadian rhythm (Knippschild et al., *Cell. Signal.* 2005, 17:675-689; Cheong and Virshup, *Int. J. Biochem. Cell Biol.* 2011, 43:465-469; Zemp, et al., *J. Cell Sci.* 2014, 127:1242-1253).

CK1α plays a role in the mitotic spindle formation during cell division and in DNA repair mechanisms and participates in RNA metabolism (Knippschild et al., Cell Signal 2005, 17:675-689). It contributes to the activation of mTOR via sustained degradation of the endogenous mTOR inhibitor DEPTOR (Duan et al., *Mol. Cell* 2011, 44:317-324).

CK1α has a major role in regulation of the Wnt/β-catenin signaling pathway. The inventors of this application have shown that CK1α is a key component of the β-catenin destruction complex. When the Wnt receptors are not engaged, CK1α phosphorylates β-catenin at serine residue S45, which is necessary for the priming phosphorylation of another kinase, GSK3 (Amit et al., *Genes Dev.* 2002, 16:1066-1076).

β-catenin phosphorylation by GSK3 at residues T41, S37 and S33, generates an ubiquitination degron, recruiting the E3 SCF-β-TrCP, leading to the ubiquitination and degradation of β-catenin (Clevers and Nusse, Cell 2012, 149:1192-1205). The inventors have further shown that inducible ablation of CK1α in the mouse gut epithelium triggers a massive epithelial Wnt response, which surprisingly did not alter intestinal homeostasis, with only little enhanced proliferation and no tumorigenesis (Elyada et al., *Nature* 2011, 470:409-413). This is dissimilar to the consequences of acute ablation of other components of the β-catenin destruction complex, such as APC, which results in loss of homeostasis and tumorigenesis (Sansom et al., *Genes Dev.* 2004, 18:1385-1390).

The inventors of the present application have found that the reason for homeostasis maintenance following CK1α ablation is that parallel to Wnt activation, CK1α ablation induces several tumor-suppressor pathways, among which are DNA damage response (DDR), cellular senescence and p53 pathway activation (Elyada et al., *Nature* 2011, 470: 409-413; Pribluda et al., *Cancer Cell* 2013, 24:1-5).

Whereas the molecular mechanisms underlying the activation of these anti-neoplastic pathways are still elusive, the inventors have found that that CK1α ablation induces disproportionally minor DNA damage, with no signs of ATM activation, indicating that CK1α-induced DDR and p53 activation likely entail uncommon molecular mechanisms (Burstain et al., unpublished). In addition, the inventors have found that CK1α ablation results in the induction of a new type of an inflammatory response, denoted parainflammation, which is confined to the epithelium, with no common signs of inflammatory response (inflammatory cell infiltration, calor, rubor, tumor, and dolor) (Pribluda et al., *Cancer Cell* 2013, 24:1-5; Lasry and Ben-Neriah, *Trends Immunol.* 2015, 36:217-228). Parainflammation cooperates with WT p53 activation in suppressing tumorigenesis, yet switches to a tumor promoting mechanism in the absence of functional p53 (Pribluda et al., *Cancer Cell* 2013, 24:1-5; Aran et al., *Genome Biol.* 2016, 17:145).

Whereas it is already established that CK1α is a major regulator of p53, the inventors have also found that the combined ablation of CK1δ and CK1ε in the gut epithelium also results in p53 activation, which may synergize with CK1α-induced p53 activation.

IRAK1 was identified as a therapeutic target for MDS, and certain subsets of AML and triple negative breast cancer (Rhyasen et al., *Cancer Cell* 2013, 24:90-104; Rhyasen et al., *Exp. Hematol.* 2013, 41:1005-7; Wee et al., *Nat. Commun.* 2015, 6:8746). IRAK1 mRNA is over-expressed in 20-30% of MDS patients and the IRAK1 protein is dramatically over-expressed and is hyperactivated in a majority of MDS marrow sample examined. IRAK1 is a serine/threonine kinase that mediates signals elicited from Toll-like receptor (TLR) and Interleukin-1 Receptor (IL1R). Following receptor activation, IRAK1 becomes phosphorylated which then leads to recruitment of TRAF6, resulting in TRAF6 activation of NF-κB and JNK pathways. The molecular source of IRAK1 overexpression and/or hyperactivation in MDS (or AML) is not conclusive. It is thought that over-expression of TLR or necessary cofactors in MDS clones may result in chronic IRAK1 activation even in the absence of infection. Small molecule inhibitors targeting IRAK1 (IRAK1/4 Inhibitor, Amgen Inc.) have been originally developed for autoimmune and inflammatory diseases. Given that IRAK1 is hyperactivated (i.e., phosphorylated) in MDS but not normal marrow cells, Starczynowski and colleagues showed that IRAK-Inhibitor treatment (IRAK1/4, Amgen) and the knockdown of IRAK1 resulted in dramatic impairment of MDS cell proliferation, progenitor function, and viability in vitro and in vivo. Yu and colleagues showed that IRAK1 overexpression confers triple negative breast cancer cells (TNBC) growth advantage through NF-κB-related cytokine secretion and metastatic TNBC cells exhibit gain of IRAK1 dependency, resulting in high susceptibility to genetic and pharmacologic inhibition of IRAK1. Paclitaxel treatment of TNBC cells induces strong IRAK1 phosphorylation, an increase in inflammatory cytokine expression, enrichment of cancer stem cells and acquired resistance to paclitaxel treatment. Pharmacologic inhibition of IRAK1 was able to reverse paclitaxel resistance by triggering massive apoptosis. IRAK1 was also found to be a DEK transcriptional target and is essential for head and neck cancer cell survival (Adams et al., *Oncotarget.* 2015, 22; 6:43395-43407) and also as potential target in the treatment of inflammatory- and immune-related disorders (Bahia et al., *Cell. Signal.* 2015, 27:1039-55).

The inventors have thus found that compounds of the invention are able to inhibit IRAK1, an important upstream regulator of the NF-kB pathway, which plays an important role in hematological malignancies.

GENERAL DESCRIPTION

The present invention provides a compound having Formula (I), or a stereoisomer or salt thereof:

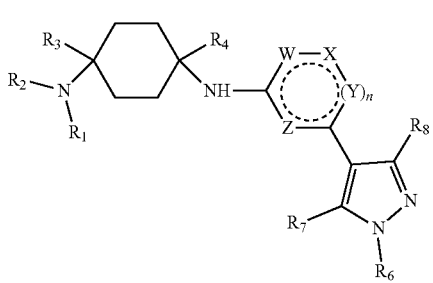

(I)

wherein:

$R_1$ and $R_2$ are each independently selected from H; and straight or branched $C_1$-$C_8$ alkyl, straight or branched $C_1$-$C_5$ alkoxy, straight or branched $C_1$-$C_5$ acyl, $C_5$-$C_{15}$ aryl, and $C_3$-$C_7$ heteroaryl, each optionally substituted by at least one of halide, hydroxyl, ester, ether, $C_5$-$C_{15}$ aryl, $C_3$-$C_7$ heteroaryl, and amide; or $R_1$ and $R_2$ together with the nitrogen atom they are connected to form a 4-7 membered saturated, unsaturated, or aromatic ring that may optionally include at least one of N, O, NH, C=N, C=O, and $SO_2$, and can optionally be substituted with at least one of straight or branched $C_1$-$C_5$ alkyl, $C_5$-$C_{15}$ aryl, $C_3$-$C_7$ heteroaryl, hydroxyl, halide, and cyano;

$R_3$ and $R_4$ are each independently selected from H and straight or branched $C_1$-$C_8$ alkyl optionally substituted by at least one of halide, hydroxyl, alkoxy, $C_5$-$C_{15}$ aryl, $C_3$-$C_7$ heteroaryl, ester, and amide; or $R_1$ or $R_2$ together with $R_3$ and the carbon and nitrogen atoms they are each connected to form a 4-7 membered saturated, unsaturated, or aromatic ring that may optionally include at least one of N, NH, O, C=N, C=O, and $SO_2$, and can optionally be substituted with at least one of straight or branched $C_1$-$C_5$ alkyl, $C_5$-$C_{15}$ aryl, $C_3$-$C_7$ heteroaryl, hydroxyl, carbonyl, and halide;

W, X, Y, and Z are each independently selected from CH, $CR_5$, $CR_{5c}$, NH, N, and S; provided that at least one of W, X, Y and Z is selected from NH, N and S; provided that, when W is N, Z is N, then X is $CR_{5c}$;

n is an integer selected from 0 and 1;

$R_5$ is selected from OH, $NH_2$, and halide;

$R_{5c}$ is selected from OH and $NH_2$;

$R_8$ is selected from H and halide; and straight or branched $C_1$-$C_8$ alkyl, straight or branched $C_2$-$C_8$ alkenyl, and straight or branched $C_2$-$C_8$ alkynyl, each optionally substituted by at least one halide;

$R_6$ is selected from straight or branched $C_1$-$C_8$ alkyl, straight or branched $C_2$-$C_8$ alkenyl, straight or branched $C_2$-$C_8$ alkynyl, $C_5$-$C_{10}$ cycloalkyl, and saturated or unsaturated 4-6 membered heterocyclyle; each optionally substituted by at least one of straight or branched $C_1$-$C_8$ alkyl, $C_3$-$C_7$ cycloalkyl, 4-6 membered heterocyclyle, $C_5$-$C_{15}$ aryl, $C_3$-$C_7$ heteroaryl, halide, hydroxyl, and $C_1$-$C_5$ alkyl halide; and $R_7$ is selected from straight or branched $C_1$-$C_8$ alkyl, straight or branched $C_2$-$C_8$ alkenyl, and straight or branched $C_2$-$C_8$ alkynyl; each independently substituted by at least one of $C_3$-$C_7$ cycloalkyl, 4-6 membered heterocyclyle, $C_5$-$C_{15}$ aryl, $C_3$-$C_7$ heteroaryl, halide, hydroxyl, and $C_1$-$C_5$ alkyl halide.

The present invention provides a compound having Formula (I), or a stereoisomer or salt thereof:

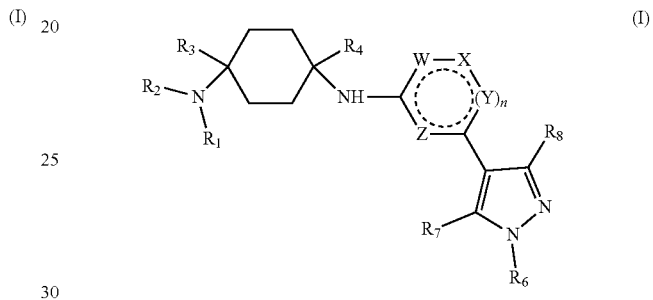

(I)

wherein:

$R_1$ and $R_2$ are each independently selected from H; and straight or branched $C_1$-$C_8$ alkyl, straight or branched $C_1$-$C_5$ alkoxy, straight or branched $C_1$-$C_5$ acyl, $C_5$-$C_{15}$ aryl, and $C_3$-$C_7$ heteroaryl, each optionally substituted by at least one of halide, hydroxyl, ester, ether, $C_5$-$C_{15}$ aryl, $C_3$-$C_7$ heteroaryl, and amide; or $R_1$ and $R_2$ together with the nitrogen atom they are connected to form a 4-7 membered saturated, unsaturated, or aromatic ring that may optionally include at least one of N, O, NH, C=N, C=O, and $SO_2$, and can optionally be substituted with at least one of straight or branched $C_1$-$C_5$ alkyl, $C_5$-$C_{15}$ aryl, $C_3$-$C_7$ heteroaryl, hydroxyl, halide, and cyano;

$R_3$ and $R_4$ are each independently selected from H and straight or branched $C_1$-$C_8$ alkyl optionally substituted by at least one of halide, hydroxyl, alkoxy, $C_5$-$C_{15}$ aryl, $C_3$-$C_7$ heteroaryl, ester, and amide; or $R_1$ or $R_2$ together with $R_3$ and the carbon and nitrogen atoms they are each connected to form a 4-7 membered saturated, unsaturated, or aromatic ring that may optionally include at least one of N, NH, O, C=N, C=O, and $SO_2$, and can optionally be substituted with at least one of straight or branched $C_1$-$C_5$ alkyl, $C_5$-$C_{15}$ aryl, $C_3$-$C_7$ heteroaryl, hydroxyl, carbonyl, and halide;

W, X, Y, and Z are each selected from CH, $CR_5$, NH, N, and S; provided that at least one of W, X, Y, and Z is selected from NH, N and S; provided that, when W is N and Z is N, then $R_8$ is other than H;

n is an integer selected from 0 and 1;

$R_5$ is selected from OH, $NH_2$, and halide;

$R_8$ is selected from H and halide; and straight or branched $C_1$-$C_8$ alkyl, straight or branched $C_2$-$C_8$ alkenyl, and straight or branched $C_2$-$C_8$ alkynyl, each optionally substituted by at least one halide;

$R_6$ is selected from straight or branched $C_1$-$C_8$ alkyl, straight or branched $C_2$-$C_8$ alkenyl, straight or branched $C_2$-$C_8$ alkynyl, $C_5$-$C_{10}$ cycloalkyl, and saturated or unsaturated 4-6 membered heterocyclyle; each optionally substituted by at least one of straight or branched $C_1$-$C_8$ alkyl, $C_3$-$C_7$ cycloalkyl, 4-6 membered heterocyclyle, $C_5$-$C_{15}$ aryl, $C_3$-$C_7$ heteroaryl, halide, hydroxyl, and $C_1$-$C_5$ alkyl halide; and $R_7$ is selected from straight or branched $C_1$-$C_8$ alkyl, straight or branched $C_2$-$C_8$ alkenyl, and straight or branched $C_2$-$C_8$ alkynyl, each independently substituted by at least one of $C_3$-$C_7$ cycloalkyl, 4-6 membered heterocyclyle, $C_5$-$C_{15}$ aryl, $C_3$-$C_7$ heteroaryl, halide, hydroxyl, and $C_1$-$C_5$ alkyl halide.

In some embodiments, $R_1$ and $R_2$ are each independently selected from H, and straight or branched $C_1$-$C_8$ alkyl optionally substituted by at least one of halide, $C_5$-$C_{15}$ aryl, $C_3$-$C_7$ heteroaryl, hydroxyl, ester, ether, and amide.

In other embodiments, $R_1$ and $R_2$ are each independently selected from H, and straight or branched $C_1$-$C_5$ alkoxy optionally substituted by at least one of halide, hydroxyl, ester, and amide.

In further embodiments, $R_1$ and $R_2$ are each independently selected from H, and $C_1$-$C_5$ acyl optionally substituted by at least one of halide, hydroxyl, ester, ether, and amide.

In some other embodiments, $R_1$ and $R_2$ are each independently selected from H and $C_5$-$C_{15}$ aryl optionally substituted by at least one of halide, hydroxyl, ester, ether, and amide.

In some embodiments, $R_4$ is H. In other embodiments, $R_3$ and $R_4$ are H.

In other embodiments, $R_5$ is halide. In some embodiments, $R_5$ is $NH_2$. In some embodiments, $R_5$ is OH.

In other embodiments, $R_8$ is selected from H, $C_1$, and straight or branched $C_1$-$C_4$ alkyl. In other embodiments, $R_8$ is H.

In some embodiments, at least one of $R_1$ and $R_2$ is H.

In some embodiments, $R_6$ selected from straight or branched $C_1$-$C_8$ alkyl, $C_5$-$C_{10}$ cycloalkyl, and saturated or unsaturated 4-6 membered heterocyclyle; and $R_7$ is selected from straight or branched $C_1$-$C_8$ alkyl, substituted by at least one of $C_3$-$C_7$ cycloalkyl, 4-6 membered heterocyclyle, $C_5$-$C_{15}$ aryl, $C_3$-$C_7$ heteroaryl, halide, hydroxyl, and $C_1$-$C_5$ alkyl halide.

In some embodiments, $R_6$ is selected from straight or branched $C_1$-$C_8$ alkyl, $C_5$-$C_{10}$ cycloalkyl, and 4-6 membered saturated heterocyclyle.

In other embodiments, $R_7$ is straight or branched $C_1$-$C_8$ alkyl substituted by at least one of $C_3$-$C_7$ cycloalkyl and hydroxyl.

In some embodiments, $R_6$ is selected from straight or branched $C_1$-$C_8$ alkyl, and saturated, unsaturated, or aromatic 4-6 membered heterocyclyle, each optionally substituted by at least one of straight or branched $C_1$-$C_8$ alkyl, $C_3$-$C_7$ cycloalkyl, halide, hydroxyl, and $CF_3$.

In some embodiments, $R_7$ is straight or branched $C_1$-$C_8$ alkyl substituted by at least one $C_3$-$C_7$ cycloalkyl.

In other embodiments, $R_1$ and $R_2$ together with the nitrogen atom they are connected to form a 4-7 membered saturated ring optionally including at least one of N, O, NH, C=N, C=O, and $SO_2$, and can optionally be substituted with at least one of straight or branched $C_1$-$C_5$ alkyl, hydroxyl, halide, and cyano.

In some embodiments, $R_1$ and $R_2$ together with the nitrogen atom they are connected to form a 4-7 membered saturated ring.

In some embodiments, $R_1$ and $R_2$ together with the nitrogen atom they are connected to form a 4-7 membered saturated ring including at least one of N and O.

In further embodiments, $R_1$ and $R_2$ together with the nitrogen atom they are connected to form a 4-7 membered aromatic ring optionally including at least one of N and O.

In other embodiments, $R_3$ and $R_4$ are H.

In some embodiments, $R_1$ or $R_2$ together with $R_3$ and the carbon and nitrogen atom they are connected to form a 4-7 membered saturated ring that optionally includes at least one of N, NH, O, C=O, and $SO_2$, and can optionally be substituted with at least one of straight or branched $C_1$-$C_5$ alkyl, hydroxyl, carbonyl, and halide.

In some embodiments, $R_1$ or $R_2$ together with $R_3$ and the carbon and nitrogen atom they are connected to form a 4-7 membered saturated ring that includes at least one of NH, O, and C=O.

In other embodiments, n is 1. When n is 1, the ring it relates to is a six membered heteroaromatic ring. In further embodiments, n is 0. When n is 0, the ring it relates to is a five membered heteroaromatic ring. Under this embodiment, when n is 0 and Y is therefore absent, X will be directly connected to the carbon atom on one side and to W on the other side.

In some embodiments, one of W, X, Y and Z is N. In further embodiments, two of W, X, Y and Z is N. In other embodiments, two of W, X, Y and Z are independently selected from NH, N, and S. In some embodiments, X is selected from CH, $CR_5$, and $CR_{5c}$. In some embodiments, W is N, Z is N, and X is $CR_{5c}$.

In some embodiments, a compounds of the invention is selected from the following, wherein $R_1$-$R_8$ are as defined herein above:

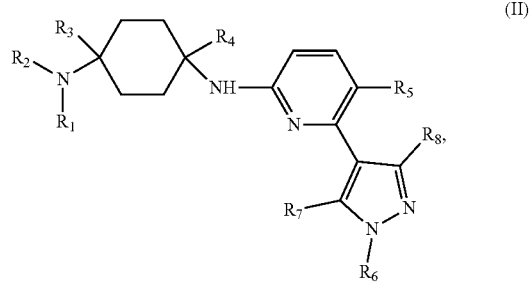

(II)

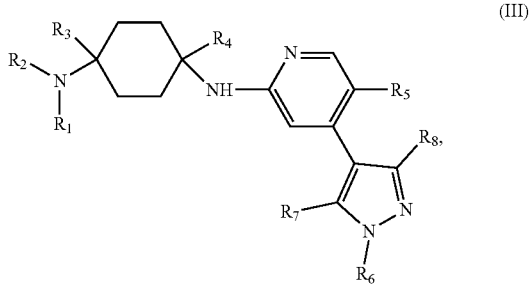

(III)

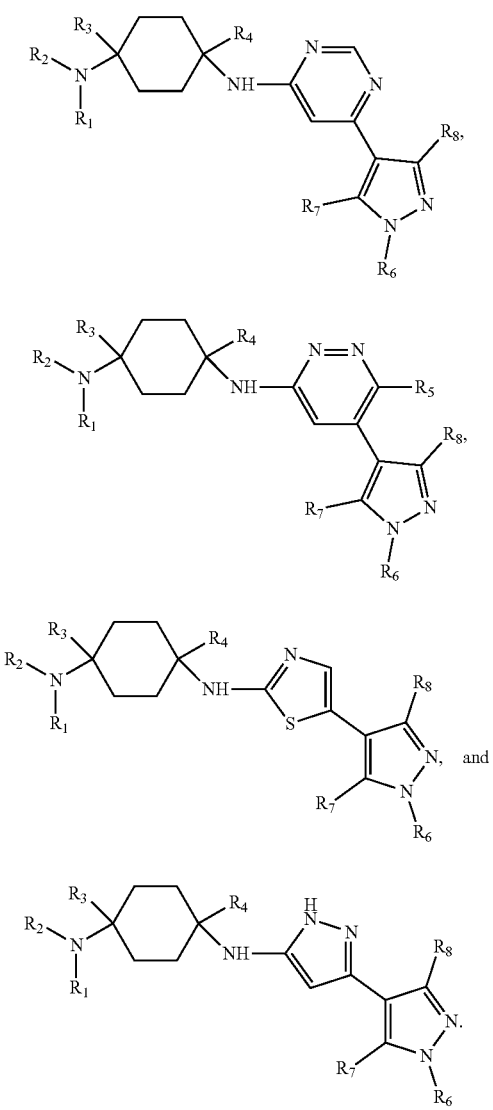

In some embodiments, a compound of the invention is selected from the following:

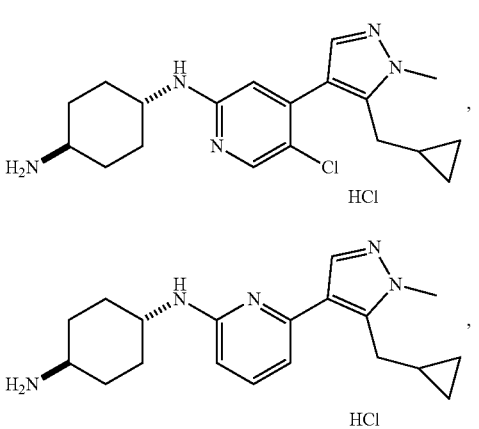

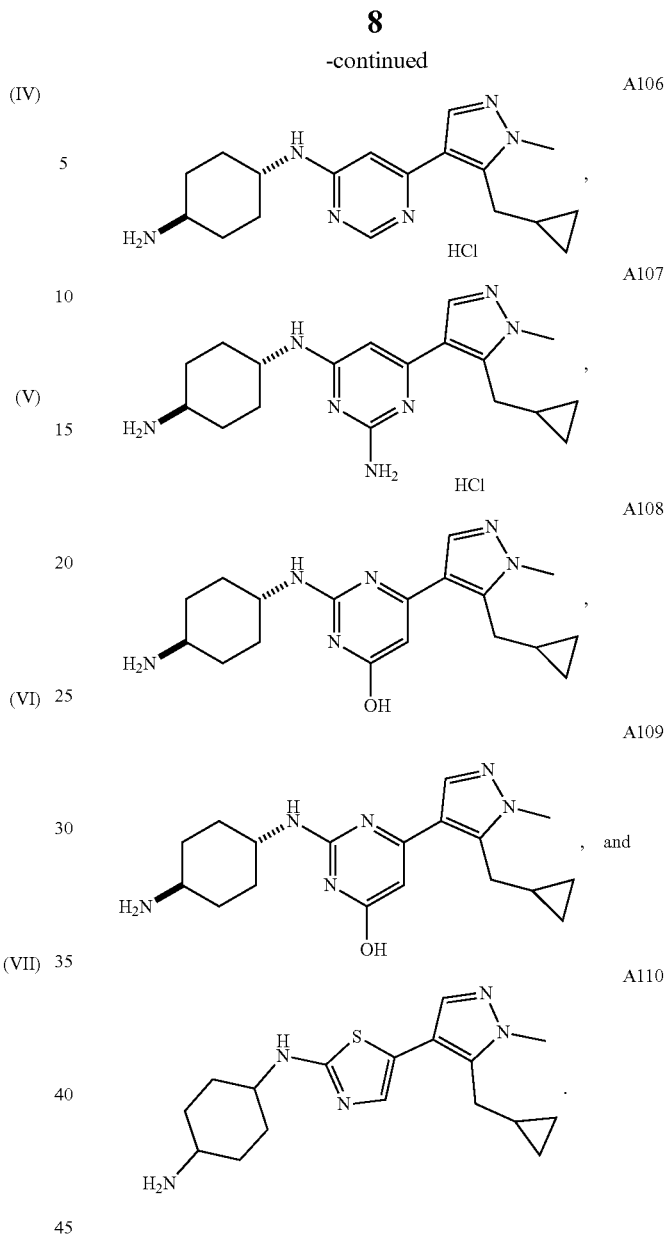

The term "straight or branched $C_1$-$C_8$ alkyl" should be understood to encompass a hydrocarbon saturated chain, which can be straight or branched, comprising 1, 2, 3, 4, 5, 6, 7, or 8 carbon atoms.

The term "straight or branched $C_2$-$C_8$ alkenyl" or "straight or branched $C_2$-$C_5$ alkenyl" should be understood to encompass a hydrocarbon chain having at least one double bond between any two adjacent carbon atoms in the chain, which can be straight or branched, comprising 2, 3, 4, 5, 6, 7, or 8 carbon atoms or 2, 3, 4, 5 carbon atoms, respectively.

The term "straight or branched $C_2$-$C_8$ alkynyl" should be understood to encompass a hydrocarbon chain having at least one triple bond between any two adjacent carbon atoms in the chain, which can be straight or branched, comprising 2, 3, 4, 5, 6, 7, or 8 carbon atoms.

The term "straight or branched $C_1$-$C_5$ alkoxy" should be understood to encompass an —$OR_9$ moiety wherein $R_9$ is straight or branched $C_1$-$C_5$ alkyl.

The term "halide" should be understood to encompass any halogen radical selected from F, —Br, —Cl, and —I.

The term "$C_1$-$C_5$ alkyl halide" should be understood to encompass any straight or branched alkyl chain having between 1 to 5 carbon atoms being substituted by at least one halogen radical selected from F, —Br, —Cl, and —I, at any point one the straight or branched chain. In some embodiments, alkyl halide includes one halogen; in other embodiments, alkyl halide includes two halogen atoms (the same or different); in other embodiments, alkyl halide includes three halogen atoms (the same or different).

The term "hydroxyl" should be understood to encompass OH.

The term "ester" should be understood to encompass any of $C(=O)OR_{10}$ or $—OC(=O)R_{10}$, wherein $R_{10}$ is straight or branched $C_1$-$C_8$ alkyl.

The term "amide" should be understood to encompass any of $C(=O)NR_{11}R_{12}'$, $—NR_{11}C(=O)R_{12}'$, wherein $R_{11}$ and $R_{12}'$ are each independently H, or straight or branched $C_1$-$C_8$ alkyl.

The term "ether" should be understood to encompass any of $R_{13}OR_{14}'$ or $OR_{15}'$, wherein $R_{13}$ is selected from straight or branched $C_1$-$C_8$ alkylene, and $R_{14}'$ and $R_{15}'$ are each independently selected from straight or branched $C_1$-$C_8$ alkyl.

The term "straight or branched $C_1$-$C_5$ acyl" should be understood to encompass any $C(=O)R_{16}$, wherein $R_{16}$ is $C_1$-$C_5$ straight or branched alkyl.

The term "$C_5$-$C_{15}$ aryl" should be understood to encompass any single or fused aromatic ring system comprising 5 to 7 carbon atoms. Examples include, but are not limited to, phenyl, pentalenyl, naphtalenyl, and anthracenyl.

The term "$C_3$-$C_7$ heteroaryl" should be understood to encompass any single or fused aromatic ring system comprising 3 to 7 carbon atoms and at least one heteroatom selected from N, O, and S. Examples include, but are not limited to, furanyl, benzofuranyl, isobenzofuranyl, pyrrolynyl, indolynyl, isoindolinyl, thiophenyl, banzothiophenyl, banzo[c]thiophenyl, imidazolyl, benzimidazolyl, purinyl, pyrazolyl, indazolyl, oxazolyl, benzoxazolyl, isoxazolyl, benzisoxazolyl, thiasolyl, benzothiazolyl, pyridinyl, auinolinyl, isoquinolinyl, pyromodinyl, quinzolinyl, pyridazinyl, and cinnolinyl.

When referring to the embodiment wherein $R_1$ and $R_2$ together with the nitrogen atom they are connected to form a 4-7 membered saturated, unsaturated, or aromatic ring, it should be understood to relate to any ring that may be formed having 4, 5, 6, or 7 members including said nitrogen atom. Said ring can be saturated, i.e., having all sigma bonds, unsaturated, i.e., having at least one double or at least one triple bond or any combinations thereof or aromatic, i.e., a ring system that possess aromatic character, cyclically conjugated molecular ring system with a stability (due to delocalization) significantly greater than that of a hypothetical localized structure (e.g., Kekulé structure).

For example, said ring can be selected from piperidinyl, pyrrolidinyl, and azetidinyl.

When referring to the embodiments wherein $R_1$ or $R_2$ together with $R_3$ and the carbon and nitrogen atom they are connected to form a 4-7 membered saturated, unsaturated or aromatic ring, it should be understood to relate to any ring that may be formed having 4, 5, 6, or 7 members including said nitrogen atom. This ring forms a spiro bi-ring system with the cyclohexyl ring in the backbone of compound of formula I. Said ring can be saturated, i.e., having all sigma bonds, or unsaturated, i.e., having at least one double or at least one triple bond or any combinations thereof. In some embodiments, the ring is an aromatic ring.

The term "$C_3Cm$ cycloalkyl" or the term "$C_3$-$C_7$ cycloalkyl" should be understood to encompass a saturated (i.e., the ring containing only sigma bonds between its members) hydrocarbon ring that comprises 5, 6, 7, 8, 9, or 10 carbon atoms or 3, 4, 5, 6, or 7 carbon atoms, respectively.

The term "saturated, unsaturated or aromatic 4-6 membered heterocyclyle" should be understood to encompass a saturated (i.e., the ring containing only sigma bonds between its members), unsaturated or aromatic (i.e., the ring containing at least one double bond or at least one triple bond or any combinations thereof) ring containing 4, 5, or 6 members at least one of which is a heteroatom selected from N, O, S, and P.

The term "optionally substituted" as used herein means that the groups in question are either unsubstituted or substituted with one or more of the substituents specified. When the groups in question are substituted with more than one substituent, the substituents may be the same or different.

Certain of the compounds described herein may contain one or more chiral center, or may otherwise be capable of existing as two enantiomers or several diastereomers. Accordingly, the compounds of this invention include also mixtures of enantiomers as well as purified enantiomers or enantiomerically enriched mixtures. The compounds of this invention include also mixtures of diastereomers, as well as purified diastereomers or diastereomerically enriched mixtures.

The invention also includes any salt of a compound of formula (I), including any pharmaceutically acceptable salt, wherein a compound of the invention has a net charge (either positive or negative) and at least one counter ion (having a counter negative or positive charge) is added thereto to form said salt. The phrase "pharmaceutically acceptable salt(s)" as used herein means those salts of compounds of the invention that are safe and effective for pharmaceutical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts, see Berge et al., *J. Pharm. Soc.* 1977, 66:1-19, incorporated herein by reference.

In some embodiments, the compound is a hydrochloride salt. In other embodiments, the compound is a monohydrochloride salt. In other embodiments, is a dihydrochloride salt.

The invention further provides a composition comprising at least one compound as defined in any one of the embodiments herein above.

The present invention also relates to pharmaceutical compositions comprising a compound of the subject invention in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association compounds of the invention or combinations thereof with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, drageés or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g., gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the therapeutic or nutritional effect to be achieved and may vary with the particular formula, the route of administration, and the age and condition of the individual subject to whom the composition is to be administered.

The term "treatment" or "therapy" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al., *Ann. Rev. Med.* 1988, 39:221-229, which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., *J. Clin. Psych.* 1984, 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. In some instances, hydrogels are biodegradable or biosorbable. For purposes of this invention, hydrogels made of polyethylene glycols, collagen, or poly(glycolic-co-L-lactic acid) may be useful. See, e.g., Phillips et al., *J. Pharmaceut. Sci.* 1984, 73:1718-1720.

The invention further provides a compound as defined in any one of the embodiments herein above for use in therapy.

The invention further provides a compound as defined in any one of the embodiments herein above for use as a medicament.

The invention provides a compound as defined in any one of the embodiments herein above, for use in the inhibition of and least one of Casein kinase I (CKI) and Interleukin-1 receptor-associated kinase 1 (IRAK1).

The invention provides a compound as defined in any one of the embodiments herein above, for use in the inhibition of Casein kinase I (CKI).

The invention provides a compound as defined in any one of the embodiments herein above, for use in the inhibition of Interleukin-1 receptor-associated kinase 1 (IRAK1).

The invention provides a compound as defined in any one of the embodiments herein above, for use in inducing anti-tumor response. In some embodiments, said anti-tumor response comprises cancer immunotherapy response.

The invention provides a compound as defined in any one of the embodiments herein above, for use in the treatment of a condition, symptom or disease associated with a malignant condition.

In some embodiments, said malignant condition is cancer. In other embodiments, malignant condition is selected from hematological malignancies, multiple myeloma, myelodysplastic syndrome (MDS), acute myeloid leukemia (AML), melanoma, ER-negative breast cancer, diffuse large B cell lymphoma (DLBCL), chronic myelogenous leukemia (CML), chronic lymphocytic leukemia (CLL), and head and neck cancer.

In some embodiments, said cancer has WT p53.

The invention provides a compound as defined in any one of the embodiments herein above, for use in the treatment of cancer having WT p53, wherein said WT p53 is a biomarker for the said compound efficacy. In some embodiments, said cancer is selected from Multiple myeloma, leukemia, malignant melanoma, breast cancer, prostate cancer, colorectal cancer and any combinations thereof.

The invention further provides a compound as defined in any one of the embodiments herein above, for use in the induction of cancer immunotherapy response.

The invention provides a compound as defined in any one of the embodiments herein above, for use in the treatment of an inflammatory and immune related disorder including a condition, symptom or disease associated therewith.

The invention provides a method of inhibiting at least one of Casein kinase I (CKI) and Interleukin-1 receptor-associated kinase 1 (IRAK1) in a subject in need thereof comprising the step of administrating to said subject at least one compound as defined in any one of the embodiments herein above.

The invention further provides a method of inhibiting casein kinase I (CKI) in a subject in need thereof comprising the step of administrating to said subject at least one compound as defined in any one of the embodiments herein above.

The invention provides a method of inhibiting interleukin-1 receptor-associated kinase 1 (IRAK1) in a subject in need thereof comprising the step of administrating to said subject at least one compound as defined in any one of the embodiments herein above.

The invention further provides a method for inducing an immunotherapy response in a subject in need thereof, said method comprising the step of administering to said subject at least one compound as defined in any one of the embodiments herein above.

The invention further provides a method of treating an inflammatory and immune related disorder, including a condition, symptom or disease associated therewith in a subject in need thereof, said method comprising the step of administering to said subject at least one compound as defined in any one of the embodiments herein above.

The term "Casein kinase I" should be understood to encompass a protein kinases family that are serine/threonine-selective enzymes that function as regulators of signal transduction pathways in most eukaryotic cell types. CK1 isoforms are involved in Wnt signaling, circadian rhythms, nucleo-cytoplasmic shuttling of transcription factors, DNA repair, p53 activation and DNA transcription.

The term "Interleukin-1 receptor-associated kinase 1" should be understood to encompass an enzyme encoded by the IRAK1 gene which was found to be an important upstream regulator of the NF-kB pathway involved in disease pathways of hematological malignancies, such as multiple myeloma, MDS, leukemia and lymphoma, breast cancer, head and neck cancer, inflammatory and immune related disorders and others.

When referring to the "inhibition" of said enzyme, it should be understood to encompass any qualitative or quantitative decrease in the activity of said enzyme due to direct or indirect binding of at least one compound of the invention to said enzyme.

The term "induced anti-tumor response" should be understood to encompass any qualitative or quantitative chemotherapy of cancerous tumors.

The term "cancer immunotherapy response" should be understood to encompass any qualitative or quantitative cancer immunotherapy induction of the subject's own immune system to fight the cancerous cells. Typically, immunotherapies can be categorized as active, passive or hybrid (active and passive), and are designed to exploit the fact that cancer cells often have molecules on their surface that can be detected by the immune system of a subject, known as tumour-associated antigens (TAAs); they are often proteins or other macromolecules (e.g., carbohydrates). Active immunotherapy directs the immune system to attack tumor cells by targeting TAAs. Passive immunotherapies enhance existing anti-tumor responses.

When referring to "inflammatory and immune related disorders" it should be understood to relate to any type of disorder (including conditions, symptoms and diseases associated therewith) that are treatable with Interleukin-1 receptor associated kinase inhibitors. It has been shown for example that IRAK1 is an indispensable element of IL-Rs and TLR pathways that can regulate the abnormal levels of cytokines, and therefore can be employed to manage immune- and inflammation-related disorders such as for example rheumatoid arthritis, inflammatory bowel disease, psoriasis, gout, asthma and cancer (Bahia et al., *Cell. Signal.* 2015, 27:1039-55).

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 shows the dose-response analysis in RKO cells. RKO cells were incubated for 16 hours at 37° C. with indicated concentrations of the compounds, or with the vehicle (DMSO) alone (−) and analyzed by Western Blot.

Shown are Western Blot signals of β-catenin and p53 stabilization and phosphorylation of H2AX (γH2AX), a marker of DNA damage.

DETAILED DESCRIPTION OF EMBODIMENTS

The invention further provides a compound of Formula I':

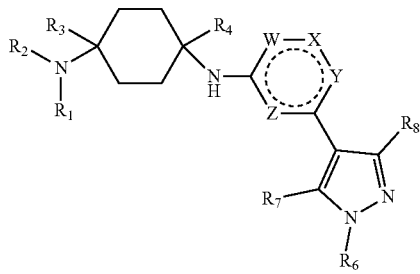

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

$R_1$ and $R_2$ are each independently H, deuterium, $C_1$-$C_8$ alkyl, $C_2$-$C_8$ alkenyl, $C_1$-$C_8$ alkynyl, $C_3$-$C_{10}$ cycloalkyl, $C_6$-$C_{15}$ aryl, $C_7$-$C_{16}$ aralkyl, heteroaryl, heterocyclyl, —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R_{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; or $R_1$ and $R_2$ together with the nitrogen atom to which they are connected form heteroaryl or heterocyclyl;

$R_3$ and $R_4$ are each independently H, deuterium, halo, cyano, nitro, $C_1$-$C_8$ alkyl, $C_2$-$C_8$ alkenyl, $C_1$-$C_8$ alkynyl, $C_3$-$C_{10}$ cycloalkyl, $C_6$-$C_{15}$ aryl, $C_7$-$C_{16}$ aralkyl, heteroaryl, or heterocyclyl; or $R_1$ and $R_3$ together with the carbon and nitrogen atoms to which they are connected form heterocyclyl;

W, X, Y, and Z are each independently $CR_{5a}$ or N, provided that, when W and Z are each N, at least one of X and Y is N; or W, X, and Z are each independently $CR_{5a}$, $NR_{5b}$, N, O, or S; and Y is a bond;

each $R_{5a}$ is independently H, deuterium, halo, cyano, nitro, $C_1$-$C_8$ alkyl, $C_2$-$C_8$ alkenyl, $C_1$-$C_8$ alkynyl, $C_3$-$C_{10}$ cycloalkyl, $C_6$-$C_{15}$ aryl, $C_7$-$C_{16}$ aralkyl, heteroaryl, heterocyclyl, —C(O)$R^{1a}$, —C(O)O$R^{1a}$, —C(O)N$R^{1b}R^{1c}$, (N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, S(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$ or —S(O)$_2$N$R^{1b}R^{1c}$;

each $R_{5b}$ is independently H, deuterium, $C_1$-$C_8$ alkyl, $C_2$-$C_8$ alkenyl, $C_1$-$C_8$ alkynyl, $C_3$-$C_{10}$ cycloalkyl, $C_6$-$C_{15}$ aryl, heteroaryl, heterocyclyl, —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O) $R^{1a}$, —OC(O)O$R^{1a}$, —OC(O)N$R^{1b}R^{1c}$, —OC(=N$R^{1a}$) N$R^{1b}R^{1c}$, —S(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;

$R_6$ is H, deuterium, $C_1$-$C_8$ alkyl, $C_2$-$C_8$ alkenyl, $C_1$-$C_8$ alkynyl, $C_3$-$C_{10}$ cycloalkyl, $C_6$-$C_{15}$ aryl, heteroaryl, heterocyclyl, —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O) N$R^{1b}R^{1c}$ or —S(O)$_2$N$R^{1b}R^{1c}$;

$R_7$ and $R_8$ are each independently H, deuterium, halo, cyano, nitro, $C_1$-$C_8$ alkyl, $C_2$-$C_8$ alkenyl, $C_1$-$C_8$ alkynyl, $C_3$-$C_{10}$ cycloalkyl, $C_3$-$C_{10}$ cycloalkyl-$C_1$-$C_8$ alkyl, $C_6$-$C_{15}$ aryl, $C_7$-$C_{16}$ aralkyl, heteroaryl, heterocyclyl, —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2$ $R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; and each $R^{1a}$, $R^{1b}$, $R^{1c}$, and $R^{1d}$ is independently H, deuterium, $C_1$-$C_8$ alkyl, $C_2$-$C_8$ alkenyl, $C_2$-$C_8$ alkynyl, $C_3$-$C_{10}$ cycloalkyl, $C_6$-$C_{15}$ aryl, $C_7$-$C_{16}$ aralkyl, heteroaryl, or heterocyclyl; or $R^{1a}$ and $R^{1c}$ together with the C and N atoms to which they are attached form heterocyclyl;

wherein each alkyl, alkenyl, alkynyl, cycloalkyl, aryl, aralkyl, heteroaryl, and heterocyclyl is optionally substituted with one or more substituents Q, where each Q is independently selected from (a) deuterium, cyano, halo, and nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{15}$ aryl, $C_7$-$C_{16}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$ N$R^aR^c$, —N$R^aR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O) $R^d$, —N$R^a$S(O)$_2R^d$, —N$R^a$S(O)N$R^bR^c$, —N$R^a$S(O)$_2$N$R^b$ $R^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen or deuterium; (ii) $C_1$-$C_8$ alkyl, $C_2$-$C_8$ alkenyl, $C_2$-$C_8$ alkynyl, $C_3$-$C_{10}$ cycloalkyl, $C_6$-$C_{15}$ aryl, $C_7$-$C_{16}$ aralkyl, heteroaryl, or heterocyclyl, each optionally substituted with one or more, in one embodiment, one, two, three, or four, substituents $Q^a$; or (iii) $R^b$ and R together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{15}$ aryl, $C_7$-$C_{16}$ aralkyl, heteroaryl, and heterocyclyl; and (c) —C(O)$R^e$, —C(O)O$R^e$, —C(O)N$R^fR^g$, —C(N$R^e$) N$R^fR^g$, —O$R^e$, —OC(O)$R^e$, —OC(O)O$R^e$, —OC(O)

NR$^f$R$^g$, —OC(=NR)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_1$-C$_8$ alkyl, C$_2$-C$_8$ alkenyl, C$_2$-C$_8$ alkynyl, C$_3$-C$_{10}$ cycloalkyl, C$_6$-C$_{15}$ aryl, C$_7$-C$_{16}$ aralkyl, heteroaryl, or heterocyclyl; or (iii) R$^f$ and R$^g$ together with the N atom to which they are attached form heterocyclyl.

In other embodiments, the compound is a compound of Formula II:

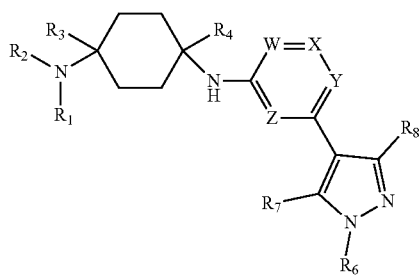

(II)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula VIII:

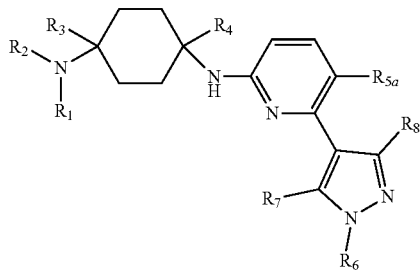

(VIII)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula IX:

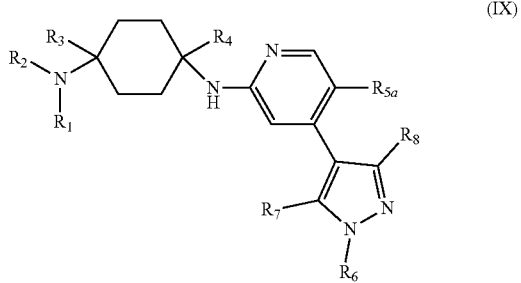

(IX)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula X:

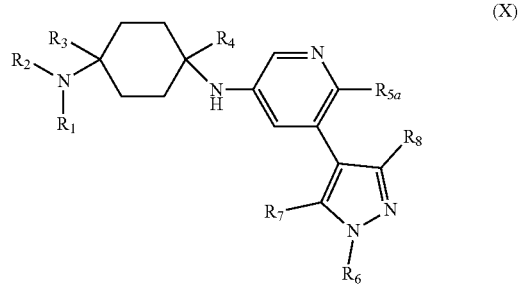

(X)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula XI:

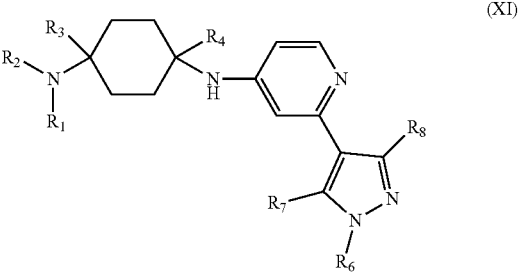

(XI)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula XII:

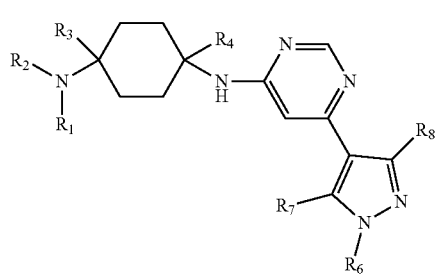
(XII)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has the following general Formula XIII:

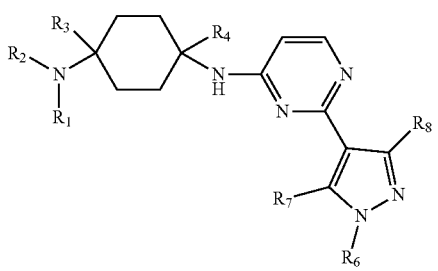
(XIII)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula XIV:

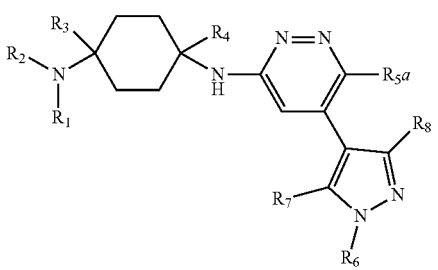
(XIV)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula XV:

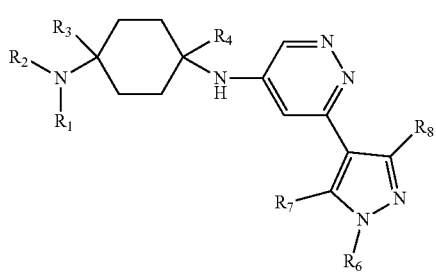
(XV)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula XVI:

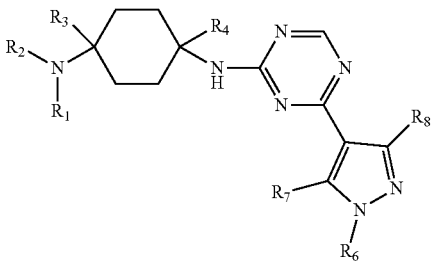
(XVI)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula XVIII:

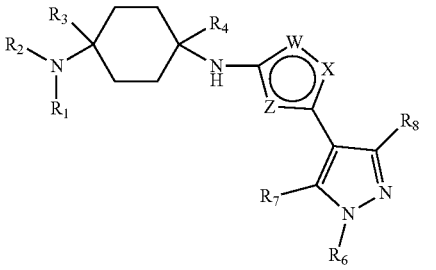
(XVIII)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula XVIII:

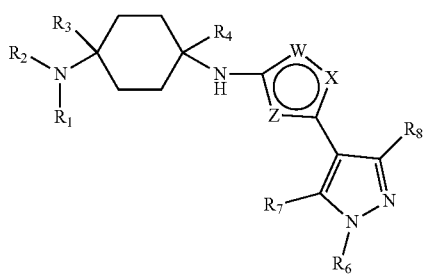

(XVIII)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula XIX:

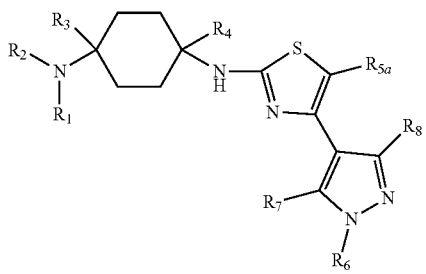

(XIX)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula XX:

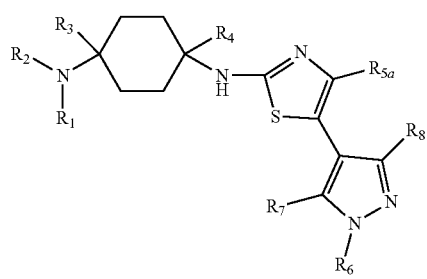

(XX)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula XXI:

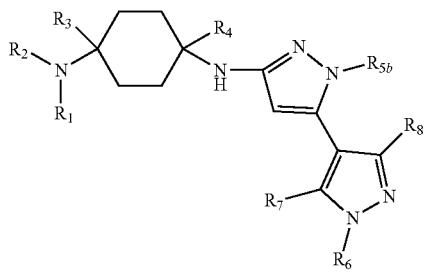

(XXI)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In other embodiments, the compound of the invention has Formula XXII:

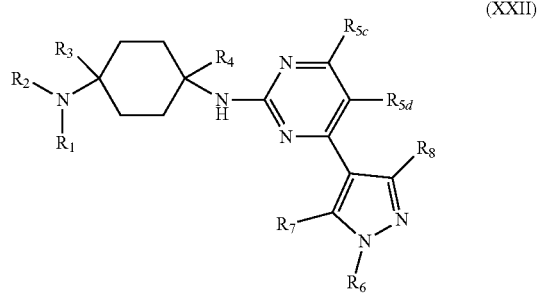

(XXII)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In some embodiments, Y is $CR_{5a}$ or N. In other embodiments, Y is $CR_{5a}$. In further embodiments, $R_{5a}$ is H, deuterium, or halo. In other embodiments, $R_{5a}$ is H, deuterium, fluoro, or chloro. In other embodiments, Y is N. In other embodiments, W is $CR_{5a}$. In other embodiments, $R_{5a}$ is H or deuterium. In other embodiments, W is N. In other embodiments, X is $CR_{5a}$. In other embodiments, $R_{5a}$ is H, deuterium, or amino. In other embodiments, X is N. In other embodiments, Z is $CR_{5a}$. In other embodiments, $R_{5a}$ is H or deuterium. In other embodiments, Z is N. In some embodiments, Y is a bond. In some embodiments, W is $CR_{5a}$. In some embodiments, $R_{5a}$ is H or deuterium. In some embodiments, W is $NR_{5b}$. In some embodiments, $R_{5b}$ is H or deuterium. In some embodiments, W is N. In some embodiments, W is O. In some embodiments, W is S. In some embodiments, X is $CR_{5a}$. In some embodiments, $R_{5a}$ is H or deuterium. In some embodiments, X is $NR_{5b}$. In some embodiments, $R_{5b}$ is H or deuterium. In some embodiments, X is N. In some embodiments, X is O. In some embodiments, X is S. In some embodiments, Z is $CR_{5a}$. In some embodiments, Z is $NR_{5b}$. In some embodiments, Z is N. In some embodiments, Z is O. In some embodiments, Z is S. In other embodiments, $R_1$ is H, deuterium, $C_1$-$C_8$ alkyl optionally substituted with one or more substituents Q, $C(O)R^{1a}$, or $C(O)OR^{1a}$. In other embodiments, $R_1$ is H. In other embodiments, $R_2$ is H, deuterium, $C_1$-$C_8$ alkyl optionally substituted with one or more substituents Q, $C(O)R^{1a}$, or $C(O)OR^{1a}$. In other embodiments, $R_2$ is H. In other embodiments, $R_3$ is H. In other embodiments, $R_4$ is H. In other embodiments, $R_6$ is H, deuterium, $C_1$-$C_8$ alkyl, $C_5$-$C_{10}$ cycloalkyl, or heterocyclyl; wherein the alkyl, cycloalkyl, heterocyclyl are each independently and optionally substituted with one or more substitutes Q. In other embodiments, $R_6$ is $C_1$-$C_8$ alkyl, $C_5$-$C_{10}$ cycloalkyl, or 4-6 membered heterocyclyl; each of which is independently and optionally substituted with one or more substitutes Q. In other embodiments, $R_6$ is $C_1$-$C_8$ alkyl, optionally substituted with one or more substitutes Q. In other embodiments, $R_6$ is methyl. In other embodiments, $R_7$ is (i) H or deuterium; or (ii) $C_1$-$C_8$ alkyl, $C_3$-$C_7$ cycloalkyl, $C_3$-$C_7$ cycloalkyl-$C_1$-$C_8$ alkyl, $C_6$-$C_{15}$ aryl, heteroaryl, or heterocyclyl, each of which is independently and optionally substituted with one or more substitutes Q. In other embodiments, $R_7$ is $C_1$-$C_8$ alkyl optionally substituted with one or more substitutes Q. In other embodiments, $R_7$ is $C_1$-$C_8$ alkyl substituted with one or more of $C_3$-$C_7$ cycloalkyl, $C_6$-$C_{15}$ aryl, heteroaryl, and heterocyclyl. In other embodiments, $R_7$ is $C_3$-$C_7$ cycloalkyl-$C_1$-$C_8$ alkyl. In other embodiments, $R_7$ is cyclopropylmethyl. In other embodiments, $R_8$ is H.

In other embodiments, a compound of the invention is selected from:

A104
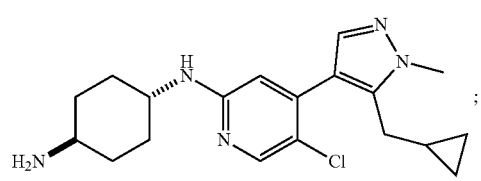

A105
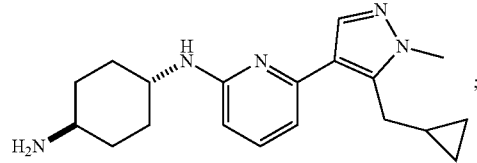

A106
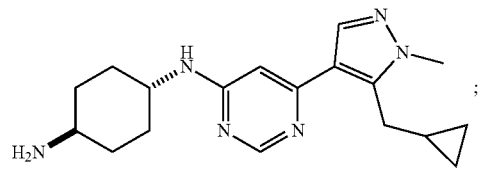

A107
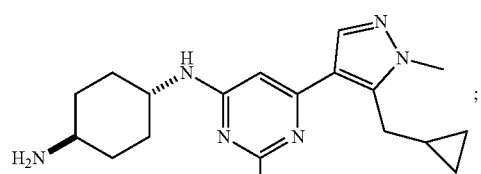

A108
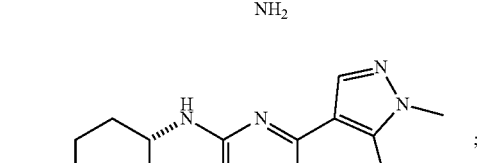

A109
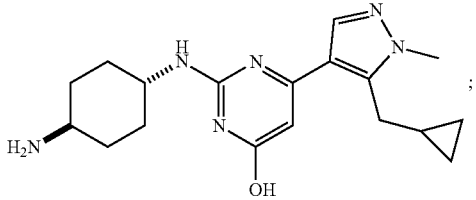

A110
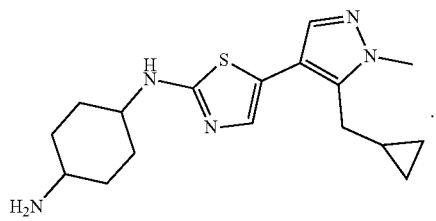

and tautomers, mixtures of two or more tautomers, and isotopic variants thereof; and pharmaceutically acceptable salts, solvates, hydrates, and prodrugs thereof.

Example 1: Synthesis of 5-(cyclopropylmethyl)-1-methyl-4-(4,4,5,5-tetramethyl-1,3,2-dioxaborolan-2-yl)-1H-pyrazole (1)

Step 1: Cyclopropyl(1-methyl-1H-pyrazol-5-yl)methanol (1-2): To a solution of compound N-methylpyrazole (1-1, 8.00 g, 97.44 mmol, 1.00 eq) in THF (160 mL) was added drop-wise n-BuLi (2.5 M, 46.77 mL, 1.20 eq) at −78° C. After 1 h at −78° C., a solution of cyclopropanecarbaldehyde (8.20 g, 116.93 mmol, 1.20 eq) in THF (80 mL) was added drop-wise. The resulting mixture was stirred at 20° C. for 16 h, poured into aqueous NH$_4$Cl (300 mL) and stirred for 10 min. The aqueous phase was extracted with ethyl acetate (100 mL×2). The combined organic phase was washed with brine (100 mL), dried over anhydrous Na$_2$SO$_4$, filtered and concentrated in vacuum. The residue was purified by column chromatography (SiO$_2$) to give compound 1-2 (12.00 g, 78.85 mmol, 80.9% yield, 100% purity) as a colorless oil. LCMS:RT=0.118 min, m/z 153.1 [M+H]$^+$.

Step 2: 5-(Cyclopropylmethyl)-1-methyl-1H-pyrazole (1-3): A mixture of compound 1-2 (9.00 g, 59.14 mmol, 1.00 eq), TFA (40.46 g, 354.84 mmol, 26.27 mL, 6.00 eq) and Et$_3$SiH (41.26 g, 354.84 mmol, 56.52 mL, 6.00 eq) in DCM (900 mL) was stirred at 40° C. for 36 h. The mixture was adjusted to pH=8 with aqueous NaHCO$_3$ and separated. The organic layer was concentrated and purified by prep HPLC (basic condition) to give compound 1-3 (2.10 g, 15.42 mmol, 26.1% yield) as a dark brown oil. LCMS:RT=0.565 min, m/z 137.1 [M+H]$^+$.

Step 3: 4-Bromo-5-(cyclopropylmethyl)-1-methyl-1H-pyrazole (1-4): To a solution of compound 1-3 (2.10 g, 15.42 mmol, 1.00 eq) in DCM (21 mL) was added NBS (3.02 g, 16.96 mmol, 1.10 eq) at 0° C. The mixture was stirred at 20° C. for 2 h, concentrated and purified by column chromatography (SiO$_2$) to give compound 1-4 (3.00 g, 13.95 mmol, 90.5% yield) as a yellow oil. LCMS:RT=0.784 min, m/z 217.1 [M+H]$^+$ $^1$H NMR (CDCl$_3$, 400 MHz) δ 7.39 (s, 1H), 3.87 (s, 3H), 2.65-2.63 (d, J=8.8 Hz, 2H), 0.98-0.94 (m, 1H), 0.55-0.51 (m, 2H), 0.29-0.25 (m, 2H).

Step 4: 5-(Cyclopropylmethyl)-1-methyl-4-(4,4,5,5-tetramethyl-1,3,2-dioxaborolan-2-yl)-1H-pyrazole (1): To a solution of compound 1-4 (3.00 g, 13.95 mmol, 1.00 eq) in THF (60 mL) was added n-BuLi (2 M, 10.46 mL, 1.50 eq) drop-wise at −78° C. After 30 min, a solution of 2-isopropoxy-4,4,5,5-tetramethyl-1,3,2-dioxaborolane (5.19 g, 27.90 mmol, 2.00 eq) in THF (6 mL) was added. The resulting mixture was warmed to 20° C. and stirred for 0.5 h, diluted with saturated NH$_4$Cl (50 mL) and extracted with EA (100 mL). The organic layer was concentrated and purified by column chromatography (SiO$_2$) to give compound 1 (3.30 g, 11.40 mmol, 81.7% yield, 90.5% purity) as a colorless oil. LCMS:RT=0.801 min, m/z 263.2 [M+H]$^+$ $^1$H NMR (CDCl$_3$, 400 MHz): δ 7.67 (s, 1H), 3.85 (s, 3H), 2.82-2.81 (d, J=6.8 Hz, 2H), 1.30 (s, 12H), 0.92-0.90 (m, 1H), 0.45-0.42 (m, 2H), 0.29-0.27 (m, 2H).

Example 2: Synthesis of (1r,4r)-N1-(5-chloro-4-(5-(cyclopropylmethyl)-1-methyl-1H-pyrazol-4-yl)pyridin-2-yl)cyclohexane-1,4-diamine (A104)

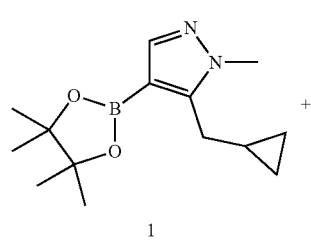

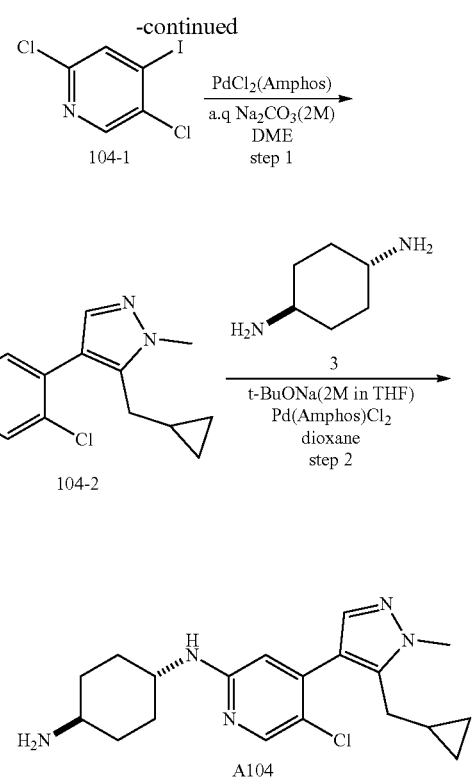

Step 1: 2,5-Dichloro-4-(5-(cyclopropylmethyl)-1-methyl-1H-pyrazol-4-yl)pyridine (104-2): To a mixture of 2,5-dichloro-4-iodopyridine (104-1, 523.13 mg, 1.91 mmol, 1.00 eq) and compound 1 (500.8 mg, 1.91 mmol, 1.0 eq) in DME (10 mL) were added Na$_2$CO$_3$ (2M, 2.87 mL, 3.00 eq) and Bis(di-tert-butyl(4-dimethylaminophenyl)phosphine)dichloro palladium (II) (67.62 mg, 95.50 μmol, 67.62 μL 0.05 eq). The resulting mixture was stirred at 80° C. for 2 h under nitrogen, cooled to room temperature, concentrated and purified by column chromatography to give 104-2 (200 mg, 659.3 μmol, 34.5% yield, 93.0% purity) as a yellow oil. LCMS:RT=0.825 min, m/z 282.0 [M+H]$^+$.

Step 2: (1r,4r)-N1-(5-Chloro-4-(5-(cyclopropylmethyl)-1-methyl-1H-pyrazol-4-yl)pyridin-2-yl)cyclohexane-1,4-diamine (A104): To a mixture of 104-2 (180.00 mg, 637.91 μmol, 1.00 eq) and (1r,4r)-cyclohexane-1,4-diamine (145.69 mg, 1.28 mmol, 2.00 eq) in dioxane (2.70 mL) was added t-BuONa (2M, 956.87 μL, 3.00 eq) and Bis(di-tert-butyl(4-dimethylaminophenyl)phosphine)dichloropalladium(II) (32.69 mg, 63.79 μmol, 0.10 eq). The mixture was stirred at 90° C. for 12 h under nitrogen, cooled to room temperature, filtered, concentrated and purified by prep-HPLC to give A104 (50 mg, 125.4 μmol, 19.7% yield, 99.4% purity, HCl) as a white solid. LCMS:RT=2.309 min, m/z 360.1 [M+H]$^+$ $^1$H NMR (MeOD, 400 MHz): δ 8.07 (s, 1H), 7.83 (s, 1H), 7.06 (s, 1H), 3.99 (s, 3H), 3.79-3.73 (m, 1H), 3.23-3.20 (m, 1H), 2.80-2.78 (d, J=6.8 Hz, 1H), 2.22-2.14 (m, 4H), 1.68-1.55 (m, 4H), 0.93-0.90 (m, 1H), 0.51-0.47 (m, 2H), 0.14-0.12 (m, 2H).

Example 3: Synthesis of (1r,4r)-N1-(6-(5-(cyclopropylmethyl)-1-methyl-1H-pyrazol-4-yl)pyridin-2-yl)cyclohexane-1,4-diamine (A105)

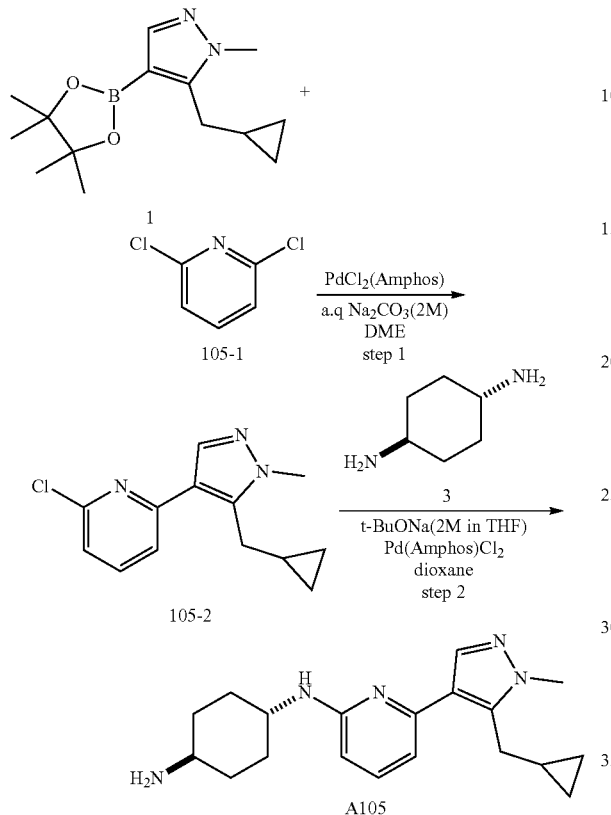

Example 4: Synthesis of (1r,4r)-N1-(6-(5-(cyclopropylmethyl)-1-methyl-1H-pyrazol-4-yl)pyrimidin-4-yl)cyclohexane-1,4-diamine (A106)

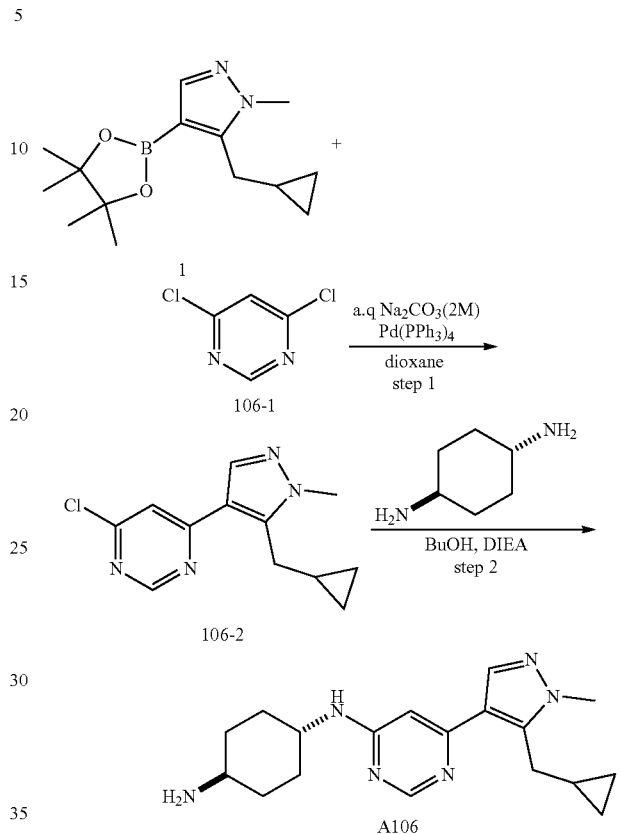

Step 1: 2-Chloro-6-(5-(cyclopropylmethyl)-1-methyl-1H-pyrazol-4-yl)pyridine (105-2): To a solution of 2,6-dichloropyridine (562 mg, 3.81 mmol, 1.00 eq) and compound 1 (1.00 g, 3.81 mmol, 1.0 eq) in DME (20 mL) was added $Na_2CO_3$ (2M, 5.72 mL, 3.00 eq) and Bis(di-tert-butyl(4-dimethylaminophenyl)phosphine)dichloropalladium (II) (134.89 mg, 190.5 umol, 134.89 uL, 0.05 eq). The mixture was stirred at 80° C. for 2 h, cooled to room temperature, concentrated and purified by column chromatography to give 105-2 (500 mg, 1.32 mmol, 34.6% yield, 74.5% purity) as a yellow oil. LCMS:RT=0.835 min, m/z 248.1 [M+H]$^+$.

Step 2: (1r,4r)-N1-(6-(5-(Cyclopropylmethyl)-1-methyl-1H-pyrazol-4-yl)pyridin-2-yl)cyclohexane-1,4-diamine (A105): To a solution of 105-2 (400.00 mg, 1.61 mmol, 1.00 eq) and (1r,4r)-cyclohexane-1,4-diamine (275.77 mg, 2.42 mmol, 1.50 eq) in dioxane (8 mL) was added t-BuONa (2M, 2.42 mL, 3.00 eq) and Bis(di-tert-butyl(4-dimethylaminophenyl)phosphine)dichloropalladium (II) (82.50 mg, 161.00 μmol, 0.10 eq). The mixture was stirred at 90° C. for 12 h, cooled to room temperature, and filtered. The filtrate was concentrated and purified by prep-HPLC to give A105 (120 mg, 331.25 μmol, 20.6% yield, 99.9% purity, HCl) as a yellow solid. LCMS:RT=2.164 min, m/z 326.2 [M+H]$^+$ 1HNMR (MeOD, 400 MHz): δ 8.01-7.97 (m, 2H), 7.10-7.08 (d, J=9.2 Hz, 1H), 6.96-6.94 (d, J=7.2 Hz, 1H), 3.96 (s, 3H), 3.79-3.77 (m, 1H), 3.22-3.17 (m, 1H), 2.92-2.91 (d, J=6.4 Hz, 1H), 2.21-2.13 (m, 4H), 1.68-1.55 (m, 4H), 0.95-0.93 (m, 1H), 0.52-0.48 (m, 2H), 0.18-0.16 (m, 2H).

Step 1: 4-Chloro-6-(5-(cyclopropylmethyl)-1-methyl-1H-pyrazol-4-yl)pyrimidine (106-2): To a solution of 4,6-dichloropyrimidine (284.5 mg, 1.91 mmol, 1.00 eq) and compound 1 (500.0 mg, 1.91 mmol, 1.00 eq) in dioxane (10 mL) was added $Na_2CO_3$ (2 M, 5.73 mL, 6.00 eq) and Pd(PPh$_3$)$_4$ (110.4 mg, 95.5 umol, 0.05 eq). The mixture was stirred at 90° C. for 2 h under nitrogen, cooled to room temperature, concentrated and purified by column chromatography to give 106-2 (200.00 mg, 562.9 μmol, 29.5% yield, 70% purity) as a colorless oil. LCMS:RT=0.784 min, m/z 249.0 [M+H]$^+$.

Step 2: (1r,4r)-N1-(6-(5-(Cyclopropylmethyl)-1-methyl-1H-pyrazol-4-yl)pyrimidin-4-yl)cyclohexane-1,4-diamine (A106): To a solution of compound 106-2 (180.0 mg, 723.73 μmol, 1.00 eq) in BuOH (1.8 mL) were added (1r,4r)-cyclohexane-1,4-diamine (165.3 mg, 1.45 mmol, 2.00 eq) and DIEA (374.1 mg, 505.59 μL 4.00 eq). The mixture was stirred at 120° C. for 16 h, cooled to room temperature, and filtered. The filtrate was concentrated and purified by prep-HPLC to give A106 (30.00 mg, 82.67 μmol, 11.4% yield, 100% purity, HCl) as a yellow solid. LCMS:RT=1.231 min, m/z 327.2 [M+H]$^+$ $^1$HNMR (MeOD, 400 MHz): δ 8.62 (s, 1H), 7.88 (s, 1H), 6.78 (s, 1H), 4.20-4.15 (m, 1H), 3.94 (s, 3H), 3.21-3.17 (m, 1H), 2.20-2.14 (m, 4H), 1.61-1.53 (m, 4H), 1.02-1.00 (m, 1H), 0.59-0.54 (m, 2H), 0.26-0.22 (m, 2H).

Example 5: Synthesis of N4-((1r,4r)-4-aminocyclohexyl)-6-(5-(cyclopropylmethyl)-1-methyl-1H-pyrazol-4-yl)pyrimidine-2,4-diamine (A107)

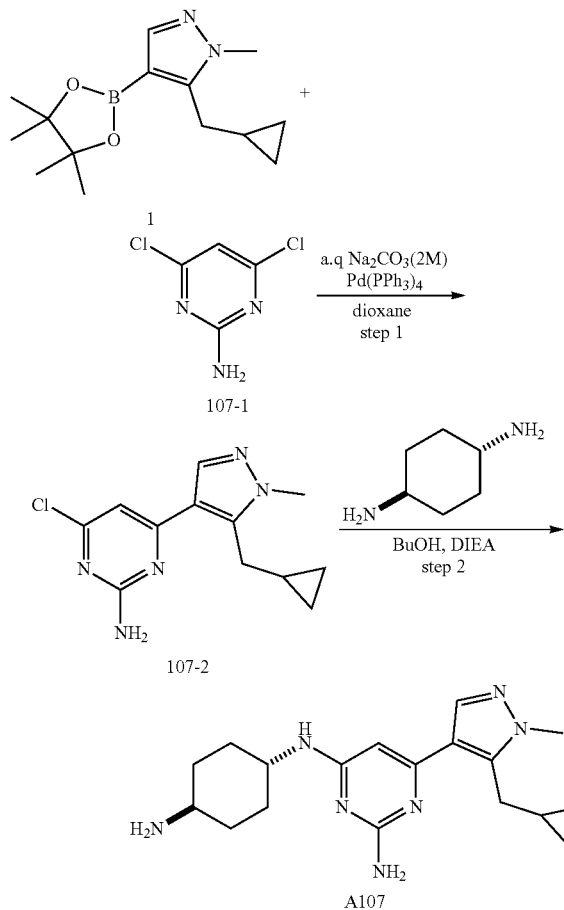

Step 1: 4-Chloro-6-(5-(cyclopropylmethyl)-1-methyl-1H-pyrazol-4-yl)pyrimidin-2-amine (107-2): To a solution of 4,6-dichloropyrimidin-2-amine (313.22 mg, 1.91 mmol, 1.00 eq) and compound 1 (500.00 mg, 1.91 mmol, 1.00 eq) in dioxane (1.0 mL) was added Na$_2$CO$_3$ (2M, 5.73 mL, 6.00 eq) and Pd(PPh$_3$)$_4$ (110.36 mg, 95.50 µmol, 0.05 eq). The mixture was stirred at 90° C. for 2 h under nitrogen, cooled to rt, concentrated and purified by column chromatography to give 107-2 (220.00 mg, 458.8 µmol, 24.0% yield, 55% purity) as a yellow solid. LCMS:RT=0.724 min, m/z 264.0 [M+H]$^+$.

Step 2: N4-((1r,4r)-4-Aminocyclohexyl)-6-(5-(cyclopropylmethyl)-1-methyl-1H-pyrazol-4-yl)pyrimidine-2,4-diamine (A107): To a solution of compound 5-2 (180.0 mg, 682.52 µmol, 1.00 eq) in BuOH (1.8 mL) were added (1r,4r)-cyclohexane-1,4-diamine (155.87 mg, 1.37 mmol, 2.00 eq) and DIEA (352.84 mg, 476.80 µL 4.00 eq). The mixture was stirred at 120° C. for 16 h, cooled to room temperature, and filtered. The filtrate was concentrated and purified by prep-HPLC to give A107 (40.00 mg, 93.86 µmol, 13.7% yield, 97.2% purity, 2HCl) as a yellow solid. LCMS: RT=2.140 min, m/z 342.2 [M+H]$^+$ $^1$HNMR (MeOD, 400 MHz) δ 7.81 (s, 1H), 6.14 (s, 1H), 4.07-4.02 (m, 1H), 3.92 (s, 3H), 3.19-3.13 (m, 1H), 2.92-2.90 (d, J=6.00 Hz, 2H), 2.19-2.12 (m, 4H), 1.60-1.45 (m, 4H), 1.00-0.99 (m, 1H), 0.56-0.53 (m, 2H), 0.24-0.20 (m, 2H).

Example 6: Synthesis of 2-(((1r,4r)-4-aminocyclohexyl)amino)-6-(5-(cyclopropylmethyl)-1-methyl-1H-pyrazol-4-yl)pyrimidin-4-ol (A108)

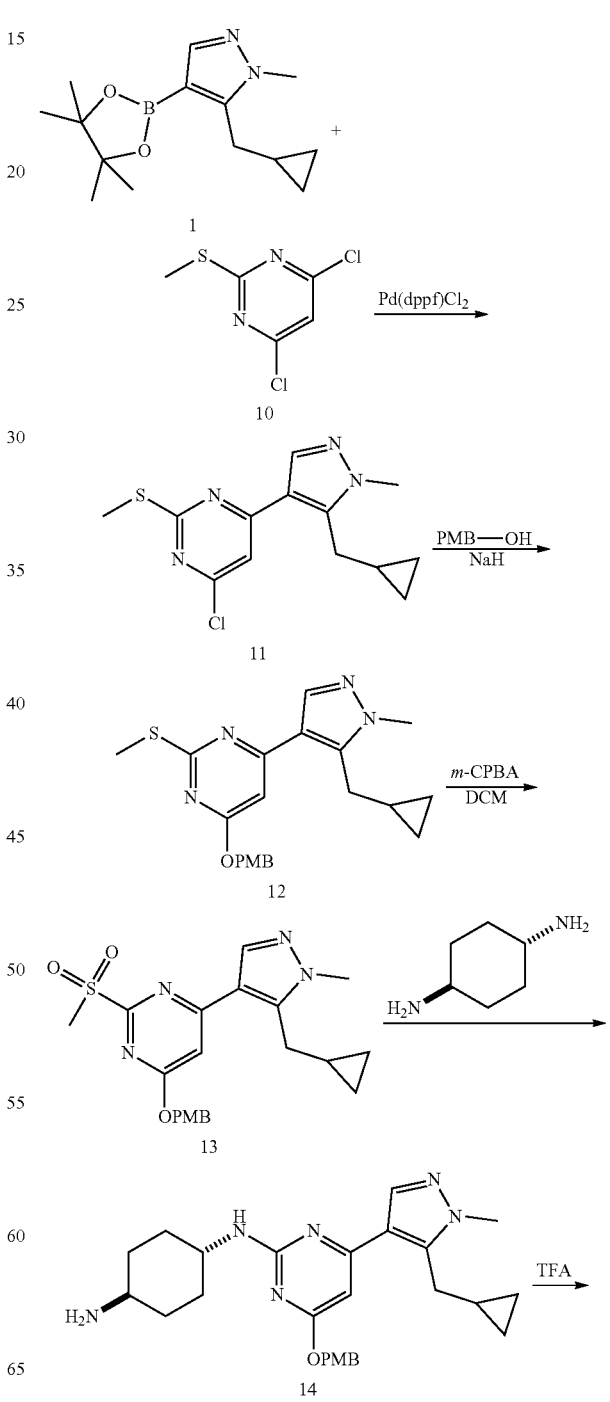

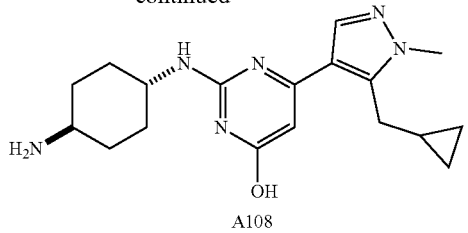

A108

Step 1: 4-Chloro-6-(5-(cyclopropylmethyl)-1-methyl-1H-pyrazol-4-yl)-2-(methylthio)pyrimidine (11): To a solution of compound 1 (1.00 g, 3.81 mmol, 1.0 eq) in dioxane (20 mL) was added compound 10 (743 mg, 3.81 mmol, 1.0 eq), Pd(dppf)C$_{12}$ (139.39 mg, 190 μmol, 0.05 eq), and Na$_2$CO$_3$ (2M, 3.81 mL, 2.0 eq) under nitrogen. The resulting mixture was stirred at 100° C. for 16 hrs under nitrogen. The mixture was filtered and the filtrate was concentrated and purified by silica gel column (PE:EA=4:1, Rf=0.4) to give compound 11 (600 mg, 1.49 mmol, 39% yield, 73% purity). LCMS: RT=0.894 min, m/z 295.0 [M+H]$^+$.

Step 2: 4-(5-(Cyclopropylmethyl)-1-methyl-1H-pyrazol-4-yl)-6-((4-methoxybenzyl)oxy)-2-(methylthio)pyrimidine (12): To a solution of PMB-OH (327 mg, 2.36 mmol, 294 μL 1.2 eq) in DMF (6 mL) was added NaH (102 mg, 2.56 mmol, 60% purity, 1.3 eq) at 0° C. After stirred for 1 hr, compound 11 (580 mg, 1.97 mmol, 1.0 eq) in THF (1.50 mL) was added drop-wise at 0° C. The resulting mixture was stirred at 20° C. for 15 hrs. The reaction was quenched with aq. NH$_4$Cl (50 mL) and extracted with EA (50 mL×2). The organic layers were concentrated and purified by silica gel column (PE:EA=10:1-5:1) to give compound 12 (140 mg, 236 μmol, 12% yield, 67% purity). LCMS:RT=0.984 min, m/z 397.0 [M+H]$^+$; $^1$HNMIR (CDCl$_3$, 400 MHz) δ 7.81 (s, 1H), 7.40-7.38 (d, J=2.4 Hz, 2H), 7.30 (m, 1H), 6.93-6.91 (m, 3H), 6.55 (s, 1H), 5.36 (s, 2H), 4.63 (s, 1H), 3.88 (s, 3H), 3.82 (s, 5H), 3.19-3.18 (d, J=6.00 Hz, 2H), 2.60 (s, 3H), 1.09-1.04 (m, 1H), 0.50-0.45 (m, 2H), 0.28-0.25 (m, 2H).

Step 3: 4-(5-(Cyclopropylmethyl)-1-methyl-1H-pyrazol-4-yl)-6-((4-methoxybenzyl)oxy)-2-(methylsulfonyl)pyrimidine (13): To a solution of compound 12 (130 mg, 328 μmol, 1.0 eq) in DCM (2.6 mL) was added m-CPBA (177 mg, 820 μmol, 80% purity, 2.5 eq) at 0° C. The mixture was stirred at 15° C. for 2 hrs. The mixture was diluted with water (10 mL) and extracted with DCM (10 mL×2). The organic layers were washed with aq. NaHCO$_3$ (10 mL). The organic layer was concentrated and purified by prep-TLC (PE:EA=1:1, Rf=0.4) to give compound 13 (80 mg, 170 μmol, 52% yield, 91% purity). LCMS:RT=0.856 min, m/z 429.0 [M+H]$^+$.

Step 4: (1r,4r)-M-(4-(5-(Cyclopropylmethyl)-1-methyl-1H-pyrazol-4-yl)-6-((4-methoxybenzyl)oxy)pyrimidin-2-yl)cyclohexane-1,4-diamine (14): To a solution of compound 13 (80 mg, 187 μmol, 1.0 eq) in dioxane (1.2 mL) was added trans-cyclohexane-1,4-diamine (85 mg, 747 μmol, 4.0 eq). The mixture was stirred at 120° C. for 2 hrs with microwave. The mixture was filtered and concentrated to give compound 14 (100 mg, crude), which was used directly for next step without further purification. LCMS:RT=0.761 min, m/z 463.3 [M+H]$^+$.

Step 5: 24(1r,4r)-4-Aminocyclohexyl)amino)-6-(5-(cyclopropylmethyl)-1-methyl-1H-pyrazol-4-yl)pyrimidin-4-ol (A108): The mixture of compound 14 (100 mg, 216 μmol, 1.0 eq) in TFA (2 mL) was stirred at 15° C. for 2 hrs. The mixture was concentrated and purified by prep-HPLC to give compound A108 (20 mg, 57 μmol, 26% yield, 98% purity). LCMS:RT=2.668 min, m/z 343.2 [M+H]$^+$; $^1$HNMR (CD$_3$OD, 400 MHz) δ 7.92 (s, 1H), 3.92 (s, 4H), 3.18-3.17 (m, 1H), 3.00 (s, 2H), 2.23-2.14 (m, 4H), 1.59-1.55 (m, 4H), 1.03 (s, 1H), 0.58-0.53 (m, 2H), 0.27-0.23 (m, 2H).

Example 7: Synthesis of (1r,4r)-N$^1$-(5-(5-(Cyclopropylmethyl)-1-methyl-1H-pyrazol-4-yl)thiazol-2-yl)cyclohexane-1,4-diamine (A110)

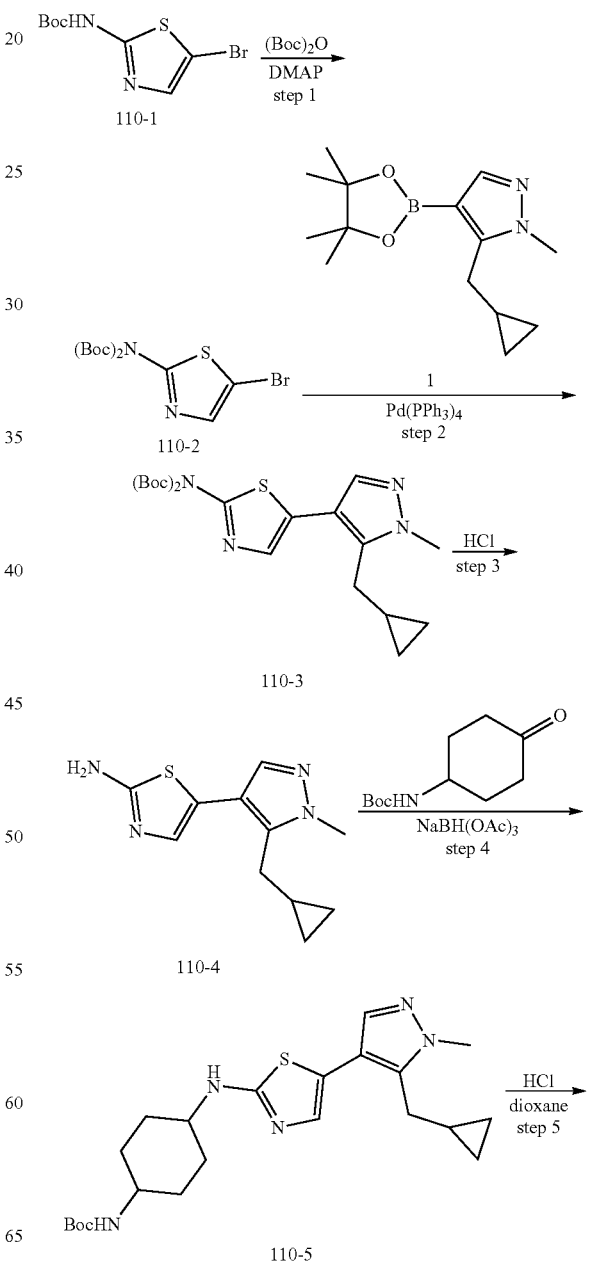

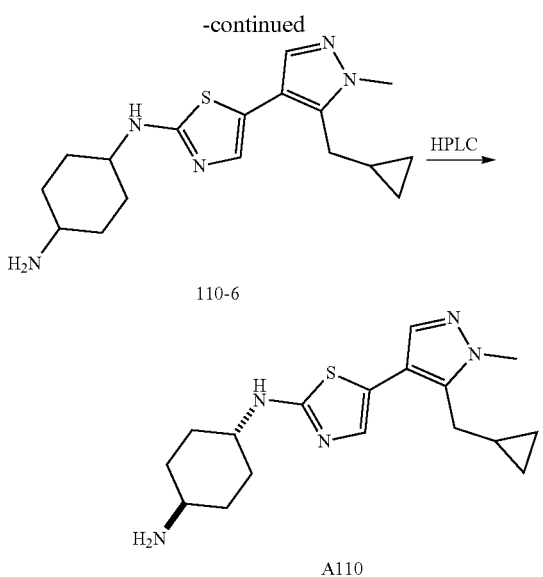

Step 1: Tert-butyl (tert-butoxycarbonyl)-(5-bromothiazol-2-yl)carbamate (110-2): To a solution of tert-butyl (5-bromothiazol-2-yl)carbamate (0.5 g, 1.79 mmol, 1.0 eq) in THF (20 mL) was added di-tert-butyl dicarbonate (0.39 g, 1.79 mmol, 1.0 eq) and DMAP (0.1 g, 0.9 mmol 0.5 eq). The resulting mixture was stirred at 60° C. for 30 min, cooled to room temperature, diluted with H$_2$O (25 mL), and extracted with EtOAc (50 mL×2). The combined organic layers were dried, filtered, concentrated, and purified by prep-TLC to give compound 110-2 (0.35 g, 0.92 mmol, 55% yield). LCMS:RT=0.944 min, m/z 379.0 [M+H]$^+$; $^1$HNMR (CDCl$_3$, 400 MHz) δ 7.40 (s, 1H), 1.54 (s, 18H).

Step 2: N,N-Bis(tert-butoxycarbonyl)-5-(5-(cyclopropylmethyl)-1-methyl-1H-pyrazol-4-yl)thiazol-2-amine (110-3): To a solution of compound 110-2 (100 mg, 0.26 mmol, 1.0 eq) in toluene (10 mL) was added compound 1 (69 mg, 0.26 mmol, 1.0 eq) and K$_2$CO$_3$ (109 mg, 0.79 mmol, 3.0 eq) under N$_2$, followed by addition of Pd(PPh$_3$)$_4$ (3.5 mg, 2.64 μmmol, 0.01 eq) under N$_2$. The reaction was heated at 110° C. for 2 hrs and cooled to room temperature. The mixture was poured into water (25 mL) and extracted with EtOAc (50 mL×2). The combined organic layers were washed with brine (10 mL), dried, filtered, concentrated, and purified by prep-TLC to give compound 110-3 (10 mg, 30 μmol, 11% yield). LCMS:RT=0.922 min, m/z 435.3 [M+H]$^+$; $^1$HNMR (CDCl$_3$, 400 MHz) δ 7.38 (m, 1H), 7.12 (m, 1H), 3.75 (s, 3H), 2.65-2.63 (m, 2H), 1.34 (s, 18H), 0.82-0.80 (m, 1H), 0.37-0.35 (m, 2H), 0.03-0.00 (m, 2H).

Step 3: 5-(5-(Cyclopropylmethyl)-1-methyl-1H-pyrazol-4-yl)thiazol-2-amine (110-4): A mixture of compound 110-3 and HCl is stirred at room temperature for 1 hr and then concentrated to give compound 110-4.

Step 4: Tert-butyl (44(5-(5-(cyclopropylmethyl)-1-methyl-1H-pyrazol-4-yl)thiazol-2-yl)amino)cyclohexyl) carbamate (110-5): To a mixture of compound 110-4 (1.0 eq) and tert-butyl (4-oxocyclohexyl)carbamate (1.0 eq) in DCM are added AcOH (1.0 eq) and NaBH(OAc)$_3$ (2.0 eq). The resulting mixture is stirred at 20° C. for 2 hrs, and then quenched with H$_2$O and worked up to give compound 110-5.

Step 5: N$^1$-(5-(5-(Cyclopropylmethyl)-1-methyl-1H-pyrazol-4-yl)thiazol-2-yl)cyclohexane-1,4-diamine (110-6): To a solution of compound 108-5 (1.0 eq) in DCM is added TFA at 0° C. The resulting mixture is stirred at 20° C. for 1 hr and then worked up to give compound 110-6, which is further purified with HPLC to give compound A110.

Example 8: Dose-Response Compound Screen in RKO Cells

RKO colorectal cells were incubated with serial dilutions of each of the compounds (at a concentration range of 0.167-1.5 μM or 0.11-1 μM in DMSO) for 16 hours at 37° C. Cells were washed with PBS and cell pellets were incubated with ice cold protein lysis buffer containing protease inhibitor cocktail (½00; Calbiochem) and phosphatase inhibitors (20 mM p-nitrophenyl phosphate (PNPP), 20 mM β-glycerophosphate and 300 nM okadaic acid). Western blot (WB) analysis was performed by means of standard techniques. Blots were incubated with antibodies detecting β-catenin (½,500; BD Transduction), p53 (DO-1&1801 hybridoma mix; dilution of 1:20 of supernatants from each), CKIα (C-19; ¹⁄₁,₀₀₀; Santa Cruz Biotechnology) and phospho-histone H2AX (S139; ¹⁄₁,₀₀₀; Millipore). Secondary antibodies were HRP-linked goat anti-mouse, goat anti-rabbit and rabbit anti-goat antibodies (all ¹⁄₁₀,₀₀₀; Jackson). Blots were developed using ECL (GE Healthcare). Signal intensities corresponding to β-catenin and p53 stabilization and phosphorylation of H2AX (γH2AX—a marker of DNA damage)-indicators of CKIα inhibition (Elyada et al., *Nature* 1991), were analyzed by the ImageJ software. Relative signal intensities are depicted in Table 1 (see also in FIG. 1), where values of 1 correspond to signals of mock (DMSO)-treated cells.

TABLE 1

Activity of Compounds of the Invention

| Cmpd. | Structure | Mass (M + H$^+$) | H2AX phosphorylation | p53 stabilization | β-Catenin stabilization |
|---|---|---|---|---|---|
| A104 | (1r,4r)-N1-(5-chloro-4-(5-(cyclopropylmethyl)-1-methyl-1H-pyrazol-4-yl)pyridin-2-yl)cyclohexane-1,4-diamine | Calc'd for C$_{19}$H$_{27}$ClN$_5$: 360.2; Found 360.1 | 20 | 20 | 9 |

TABLE 1-continued

Activity of Compounds of the Invention

| Cmpd. | Structure | Mass (M + H⁺) | H2AX phosphorylation | p53 stabilization | β-Catenin stabilization |
|---|---|---|---|---|---|
| A105 | (1r,4r)-N1-(6-(5-(cyclopropylmethyl)-1-methyl-1H-pyrazol-4-yl)pyridin-2-yl)cyclohexane-1,4-diamine | Calc'd for $C_{19}H_{28}N_5$: 326.2; Found 326.2 | 1 | 2 | 5 |
| A106 | (1r,4r)-N1-(6-(5-(cyclopropylmethyl)-1-methyl-1H-pyrazol-4-yl)pyrimidin-4-yl)cyclohexane-1,4-diamine | Calc'd for $C_{19}H_{27}N_6$: 327.2; Found: 327.2 | 1 | 1 | 9 |
| A107 | N4-((1r,4r)-4-aminocyclohexyl)-6-(5-(cyclopropyl-methyl)-1H-pyrazol-4-yl)pyrimidine-2,4-diamine | Calc'd for $C_{19}H_{28}N_7$: 342.2; Found: 342.2 | 1 | 2 | 4 |
| A108 | 2-(((1r,4r)-4-aminocyclohexyl)amino)-6-(5-(cyclopropyl-methyl)-1-methyl-1H-pyrazol-4-yl)pyrimidin-4-ol | Calc'd for $C_{18}H_{27}ClN_6O$: 378.9; Found: 378.9 | 1 | 1 | 9 |
| A102 | 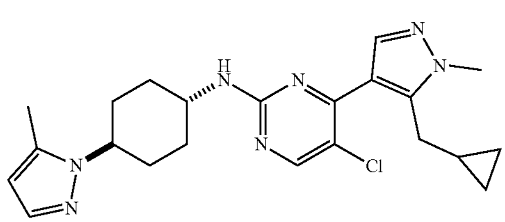 | Calc'd for $C_{22}H_{29}Cl_2N_7$: 462.42; Found: 462.42 | 1 | 1 | 4 |

The invention claimed is:
1. A compound of Formula (I):

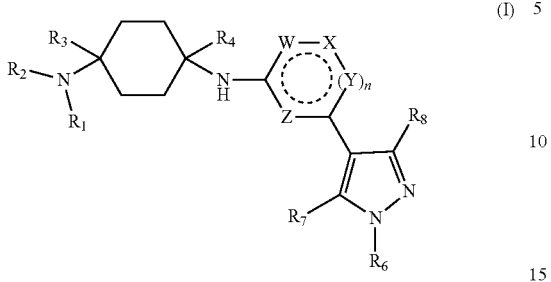

or a stereoisomer or a pharmaceutically acceptable salt thereof;
wherein:
- $R_1$ and $R_2$ are each independently selected from H; and straight or branched $C_1$-$C_8$ alkyl, straight or branched $C_1$-$C_5$ alkoxy, —C(O)-(straight or branched $C_1$-$C_5$ alkyl), phenyl, naphthyl, anthracenyl, and $C_3$-$C_7$ heteroaryl, each optionally substituted by at least one of halide, hydroxyl, —C(O)OR$_{10}$, —OC(O)R$_{10}$, —R$_{13}$OR$_{14'}$, —OR$_{15'}$, phenyl, naphthyl, anthracenyl, $C_3$-$C_7$ heteroaryl, —C(O)NR$_{11}$R$_{12'}$, and —NR$_{11}$C(O)R$_{12'}$; or
- $R_1$ and $R_2$ together with the nitrogen atom they are connected to form a 4-7 membered saturated, unsaturated, or aromatic ring that optionally comprises at least one of N, O, NH, C=O, and SO$_2$, and is optionally substituted with at least one of straight or branched $C_1$-$C_5$ alkyl, phenyl, naphthyl, anthracenyl, $C_3$-$C_7$ heteroaryl, hydroxyl, halide, and cyano;
- $R_3$ and $R_4$ are each independently selected from H, and straight or branched $C_1$-$C_8$ alkyl optionally substituted by at least one of halide, hydroxyl, $C_1$-$C_5$ alkoxy, phenyl, naphthyl, anthracenyl, $C_3$-$C_7$ heteroaryl, —C(O)OR$_{10}$, —OC(O)R$_{10}$, —C(O)NR$_{11}$R$_{12'}$, and —NR$_{11}$C(O)R$_{12'}$; or
- $R_1$ or $R_2$ together with $R_3$ and the carbon and nitrogen atoms they are each connected to form a 4-7 membered saturated, unsaturated, or aromatic ring that optionally comprises includes at least one of N, NH, O, C=O, and SO$_2$, and is optionally substituted with at least one of straight or branched $C_1$-$C_5$ alkyl, phenyl, naphthyl, anthracenyl, $C_3$-$C_7$ heteroaryl, hydroxyl, and halide;
- W, X, Y, and Z are each independently selected from CH, CR$_5$, CR$_{5c}$, NH, N, and S; provided that at least one of W, X, Y and Z is selected from NH, N, and S; and provided that, when W is N and Z is N, then X is CR$_{5c}$;
- n is an integer of 0 or 1;
- $R_5$ is selected from OH, NH$_2$, and halide; $R_{5'}$ is OH or NH$_2$;
- $R_8$ is selected from H and halide; and straight or branched $C_1$-$C_8$ alkyl, straight or branched $C_2$-$C_8$ alkenyl, and straight or branched $C_2$-$C_8$ alkynyl, each optionally substituted by at least one halide;
- $R_6$ is selected from straight or branched $C_1$-$C_8$ alkyl, straight or branched $C_2$-$C_8$ alkenyl, straight or branched $C_2$-$C_8$ alkynyl, $C_5$-$C_{10}$ cycloalkyl, and saturated or unsaturated 4-6 membered heterocyclyl, each optionally substituted by at least one of straight or branched $C_1$-$C_8$ alkyl, $C_3$-$C_7$ cycloalkyl, 4-6 membered heterocyclyl, phenyl, naphthyl, anthracenyl, $C_3$-$C_7$ heteroaryl, halide, hydroxyl, and $C_1$-$C_5$ haloalkyl;
- $R_7$ is selected from straight or branched $C_1$-$C_8$ alkyl, straight or branched $C_2$-$C_8$ alkenyl, and straight or branched $C_2$-$C_8$ alkynyl, each independently substituted by at least one of $C_3$-$C_7$ cycloalkyl, 4-6 membered heterocyclyl, phenyl, naphthyl, anthracenyl, $C_3$-$C_7$ heteroaryl, halide, hydroxyl, and $C_1$-$C_5$ haloalkyl;
- each $R_{10}$ is independently straight or branched $C_1$-$C_8$ alkyl;
- each $R_{11}$ and $R_{12'}$ is independently H, or straight or branched $C_1$-$C_8$ alkyl;
- each $R_{13}$ is independently straight or branched $C_1$-$C_8$ alkylene; and
- each $R_{14'}$ and $R_{15'}$ is independently H, or straight or branched $C_1$-$C_8$ alkyl;
- wherein each heteroaryl independently comprises at least one heteroatom selected from N, O, and S and each heterocyclyl independently comprises at least one heteroatom selected from N, O, and S.

2. The compound according to claim 1, wherein $R_1$ and $R_2$ are each independently selected from H, and straight or branched $C_1$-$C_8$ alkyl optionally substituted by at least one of halide, phenyl, naphthyl, anthracenyl, $C_3$-$C_7$ heteroaryl, hydroxyl, an ester, an ether, and an amide.

3. The compound according to claim 1, wherein $R_4$ is H.

4. The compound according to claim 1, wherein $R_3$ and $R_4$ are each H.

5. The compound according to claim 1, wherein $R_5$ is halide.

6. The compound according to claim 1, wherein $R_5$ is NH$_2$.

7. The compound according to claim 1, wherein $R_5$ is OH.

8. The compound according to claim 1, wherein $R_8$ is selected from H, Cl, and straight or branched $C_1$-$C_4$ alkyl.

9. The compound according to claim 1, wherein $R_8$ is H.

10. The compound according to claim 1, wherein at least one of $R_1$ and $R_2$ is H.

11. The compound according to claim 1, wherein $R_6$ is selected from straight or branched $C_1$-$C_8$ alkyl, $C_5$-$C_{10}$cycloalkyl, and saturated or unsaturated 4-6 membered heterocyclyl; and $R_7$ is selected from straight or branched $C_1$-$C_8$ alkyl, substituted by at least one of $C_3$-$C_7$ cycloalkyl, 4-6 membered heterocyclyl, phenyl, naphthyl, anthracenyl, $C_3$-$C_7$ heteroaryl, halide, hydroxyl, and $C_1$-$C_5$ haloalkyl.

12. The compound according to claim 1, wherein $R_6$ is selected from straight or branched $C_1$-$C_8$ alkyl, $C_5$-$C_{10}$cycloalkyl, and 4-6 membered saturated heterocyclyl.

13. The compound according to claim 1, wherein $R_7$ is straight or branched $C_1$-$C_8$ alkyl substituted by at least one of $C_3$-$C_7$ cycloalkyl and hydroxyl.

14. The compound according to claim 1, wherein $R_6$ is straight or branched $C_1$-$C_8$ alkyl, l each optionally substituted by at least one of straight or branched $C_1$-$C_8$ alkyl, $C_3$-$C_7$ cycloalkyl, halide, hydroxyl, and CF$_3$.

15. The compound according to claim 1, wherein $R_7$ is straight or branched $C_1$-$C_8$ alkyl substituted by at least one $C_3$-$C_7$ cycloalkyl.

16. The compound according to claim 1, wherein n is an integer of 1.

17. The compound according to claim 1, wherein n is an integer of 0.

18. The compound according to claim 1, wherein one of W, X, Y, and Z is N.

19. The compound according to claim 1, wherein two of W, X, Y, and Z is N.

20. The compound according to claim 17, wherein two of W, X, Y, and Z are each independently selected from NH, N, and S.

21. The compound according to claim 1, selected from:

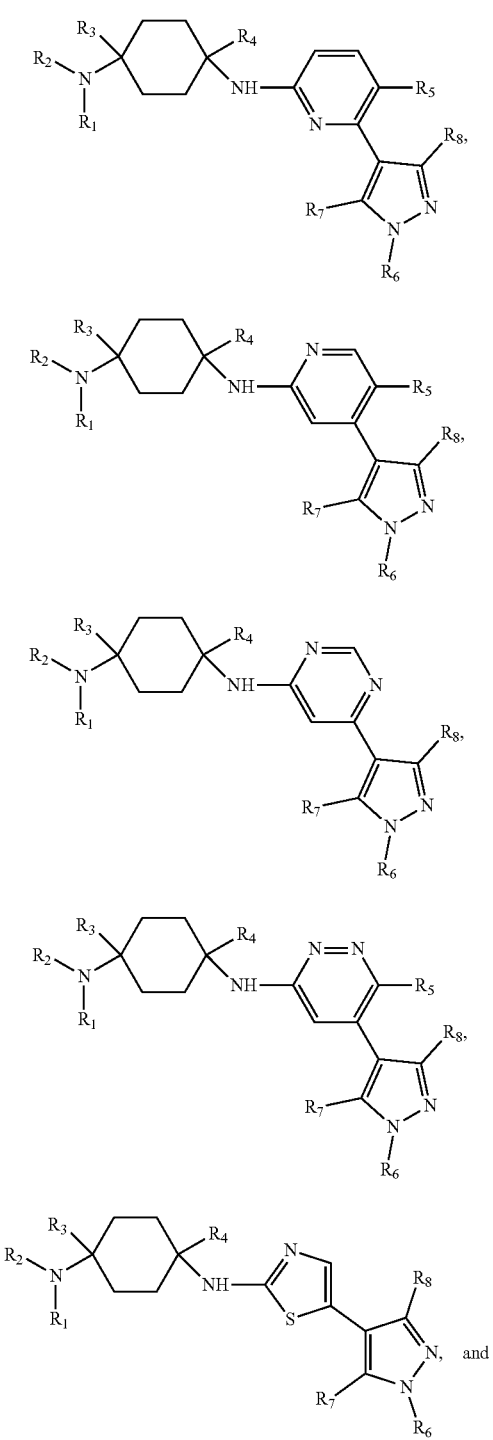

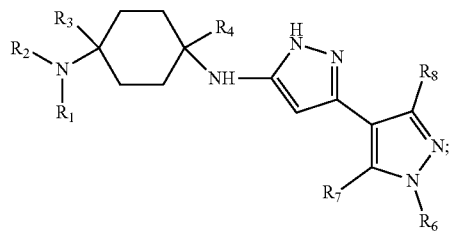

and stereoisomers and pharmaceutically acceptable salts thereof.

22. A compound selected from:

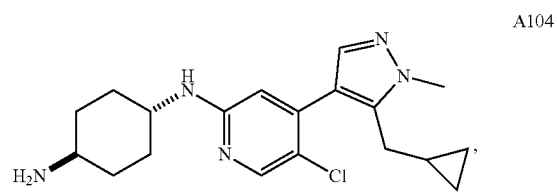

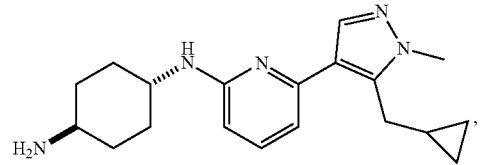

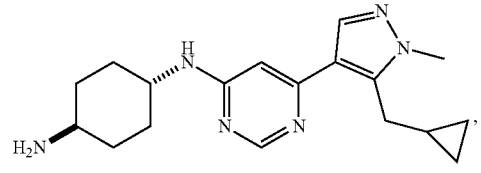

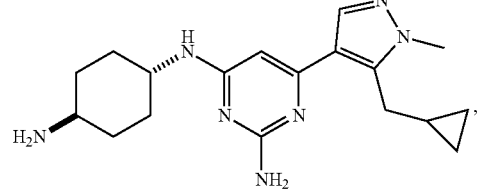

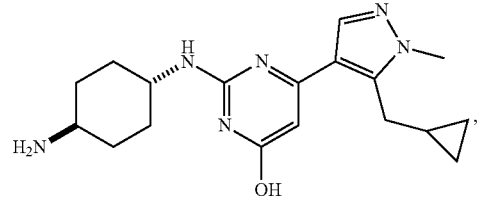

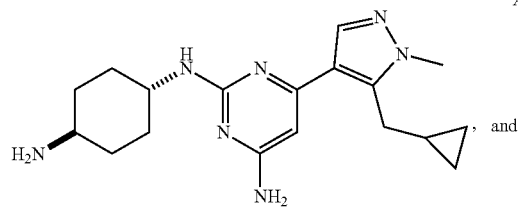

-continued

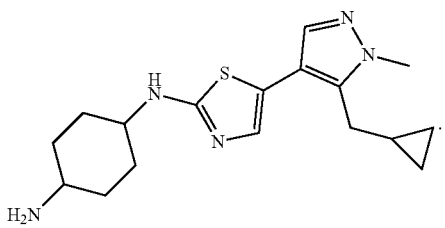

A110

23. A pharmaceutical composition comprising a therapeutically effective amount of a compound, or a stereoisomer or a pharmaceutically acceptable salt thereof according to claim 1; and a pharmaceutically acceptable excipient.

24. A compound of Formula (IA):

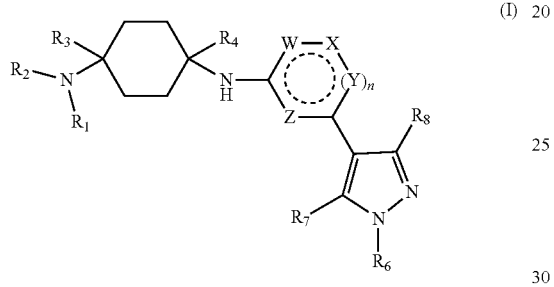

(I)

or a stereoisomer or a pharmaceutically acceptable salt thereof;
wherein:
$R_1$ and $R_2$ are each independently selected from H; and straight or branched $C_1$-$C_8$ alkyl, straight or branched $C_1$-$C_5$ alkoxy, —C(O)-(straight or branched $C_1$-$C_5$ alkyl), phenyl, naphthyl, anthracenyl, and $C_3$-$C_7$ heteroaryl, each optionally substituted by at least one of halide, hydroxyl, —C(O)OR$_{10}$, —OC(O)R$_{10}$, —R$_{13}$OR$_{14'}$, —OR$_{15'}$, phenyl, naphthyl, anthracenyl, $C_3$-$C_7$ heteroaryl, —C(O)NR$_{11}$R$_{12'}$, and —NR$_{11}$C(O)R$_{12'}$; or $R_1$ and $R_2$ together with the nitrogen atom they are connected to form a 4-7 membered saturated, unsaturated, or aromatic ring that optionally comprises at least one of N, O, NH, C=O, and SO$_2$, and is optionally substituted with at least one of straight or branched $C_1$-$C_5$ alkyl, phenyl, naphthyl, anthracenyl, $C_3$-$C_7$ heteroaryl, hydroxyl, halide, and cyano;

$R_3$ and $R_4$ are each independently selected from H, and straight or branched $C_1$-$C_8$ alkyl optionally substituted by at least one of halide, hydroxyl, alkoxy, phenyl, naphthyl, anthracenyl, $C_3$-$C_7$ heteroaryl, —C(O)OR$_{10}$, —OC(O)R$_{10}$, —C(O)NR$_{11}$R$_{12'}$, and —NR$_{11}$C(O)R$_{12'}$; or $R_1$ or $R_2$ together with $R_3$ and the carbon and nitrogen atoms they are each connected to form a 4-7 membered saturated, unsaturated, or aromatic ring that optionally comprises at least one of N, NH, O, C=O, and SO$_2$, and is optionally substituted with at least one of straight or branched $C_1$-$C_5$ alkyl, phenyl, naphthyl, anthracenyl, $C_3$-$C_7$ heteroaryl, hydroxyl, and halide;

W, X, Y, and Z are each independently selected from CH, CR$_5$, NH, N, and S; provided that at least one of W, X, Y and Z is selected from NH, N and S; provided that, when W is N and Z is N, then R$_8$ is other than H;

n is an integer of 0 or 1;

$R_5$ is selected from OH, NH$_2$, and halide;

$R_8$ is selected from H and halide; and straight or branched $C_1$-$C_8$ alkyl, straight or branched $C_2$-$C_8$ alkenyl, and straight or branched $C_2$-$C_8$ alkynyl, each optionally substituted by at least one halide;

$R_6$ is selected from straight or branched $C_1$-$C_8$ alkyl, straight or branched $C_2$-$C_8$ alkenyl, straight or branched $C_2$-$C_8$ alkynyl, $C_5$-$C_{10}$ cycloalkyl, and saturated or unsaturated 4-6 membered heterocyclyl, each optionally substituted by at least one of straight or branched $C_1$-$C_8$ alkyl, $C_3$-$C_7$ cycloalkyl, 4-6 membered heterocyclyl, phenyl, naphthyl, anthracenyl, $C_3$-$C_7$ heteroaryl, halide, hydroxyl, and $C_1$-$C_5$ haloalkyl;

$R_7$ is selected from straight or branched $C_1$-$C_8$ alkyl, straight or branched $C_2$-$C_8$ alkenyl, and straight or branched $C_2$-$C_8$ alkynyl, each independently substituted by at least one of $C_3$-$C_7$ cycloalkyl, 4-6 membered heterocyclyl, phenyl, naphthyl, anthracenyl, $C_3$-$C_7$ heteroaryl, halide, hydroxyl, and $C_1$-$C_5$ haloalkyl;

each $R_{10}$ is independently straight or branched $C_1$-$C_8$ alkyl;

each $R_{11}$ and $R_{12'}$ is independently H, or straight or branched $C_1$-$C_8$ alkyl;

each $R_{13}$ is independently straight or branched $C_1$-$C_8$ alkylene; and each $R_{14'}$ and $R_{15'}$ is independently H, or straight or branched $C_1$-$C_8$ alkyl;

wherein each heteroaryl independently comprises at least one heteroatom selected from N, O, and S and each heterocyclyl independently comprises at least one heteroatom selected from N, O, and S.

25. A compound selected from:
(1r,4r)-N$^1$-(5-chloro-4-(5-(cyclopropylmethyl)-1-methyl-1H-pyrazol-4-yl)pyridin-2-yl)cyclohexane-1,4-diamine;
(1r,4r)-N$^1$-(6-(5-(cyclopropylmethyl)-1-methyl-1H-pyrazol-4-yl)pyridin-2-yl)cyclohexane-1,4-diamine;
(1r,4r)-N$^1$-(6-(5-(cyclopropylmethyl)-1-methyl-1H-pyrazol-4-yl)pyrimidin-4-yl)cyclohexane-1,4-diamine;
N$^4$-((1r,4r)-4-aminocyclohexyl)-6-(5-(cyclopropylmethyl)-1-methyl-1H-pyrazol-4-yl)pyrimidine-2,4-diamine;
2-(((1r,4r)-4-aminocyclohexyl)amino)-6-(5-(cyclopropylmethyl)-1-methyl-1H-pyrazol-4-yl)pyrimidin-4-ol;
N$^2$-((1r,4r)-4-aminocyclohexyl)-6-(5-(cyclopropylmethyl)-1-methyl-1H-pyrazol-4-yl)pyrimidine-2,4-diamine; and
(1r,4r)-N$^1$-(5-(5-(cyclopropylmethyl)-1-methyl-1H-pyrazol-4-yl)thiazol-2-yl)cyclohexane-1,4-diamine;
and stereoisomers and pharmaceutically acceptable salts thereof.

* * * * *